(12) United States Patent
Morgan et al.

(10) Patent No.: US 8,794,051 B2
(45) Date of Patent: Aug. 5, 2014

(54) COMBINED RHEOMETER/MIXER HAVING HELICAL BLADES AND METHODS OF DETERMINING RHEOLOGICAL PROPERTIES OF FLUIDS

(75) Inventors: Ronnie Glen Morgan, Waurika, OK (US); Sairam KS Pindiprolu, Pune (IN); Balasundaram Balaraman, Pune (IN); Ganesh Shriniwas Pangu, Talegaon Dabhade (IN)

(73) Assignee: Halliburton Energy Services, Inc., Houston, TX (US)

( * ) Notice: Subject to any disclaimer, the term of this patent is extended or adjusted under 35 U.S.C. 154(b) by 248 days.

(21) Appl. No.: 13/293,469

(22) Filed: Nov. 10, 2011

(65) Prior Publication Data
US 2013/0118235 A1 May 16, 2013

(51) Int. Cl.
*G01N 11/14* (2006.01)

(52) U.S. Cl.
USPC ....... 73/54.28; 73/54.01; 73/54.02; 73/54.23; 73/54.31

(58) Field of Classification Search
USPC ............ 73/53.01, 54.01, 54.02, 54.23, 54.28, 73/54.31
See application file for complete search history.

(56) References Cited

U.S. PATENT DOCUMENTS

| | | | |
|---|---|---|---|
| 3,362,487 A | 1/1968 | Lindsey | |
| 3,429,385 A | 2/1969 | Jones et al. | |
| 3,443,643 A | 5/1969 | Jones | |
| 3,883,359 A * | 5/1975 | Harvey | 501/124 |
| 4,234,043 A | 11/1980 | Roberts | |
| 4,436,157 A | 3/1984 | Brooks | |
| 4,668,911 A | 5/1987 | Mueller | |
| 4,682,913 A | 7/1987 | Shatto et al. | |
| 4,685,521 A | 8/1987 | Raulins | |
| 5,209,108 A * | 5/1993 | Shackelford | 73/54.28 |
| 5,708,197 A * | 1/1998 | Todd et al. | 73/54.28 |
| 5,771,974 A | 6/1998 | Stewart et al. | |
| 6,782,735 B2 * | 8/2004 | Walters et al. | 73/54.28 |
| 6,874,353 B2 | 4/2005 | Johnson et al. | |
| 6,892,812 B2 | 5/2005 | Niedermayr et al. | |
| 6,920,942 B2 | 7/2005 | Koederitz | |
| 7,712,526 B2 * | 5/2010 | Morgan et al. | 166/250.1 |
| 7,832,257 B2 * | 11/2010 | Weightman et al. | 73/54.09 |
| 7,992,427 B2 * | 8/2011 | Tonmukayakul et al. | 73/54.28 |
| 8,201,628 B2 | 6/2012 | Lovorn et al. | |
| 8,230,723 B2 * | 7/2012 | Moon et al. | 73/54.28 |

(Continued)

OTHER PUBLICATIONS

A. Thesing, New Device for Rheology Measurements of Proppant-Laden Fluids With the Fann 50 Viscometer, SPE 58759, 2000.*

(Continued)

*Primary Examiner* — David A Rogers
(74) *Attorney, Agent, or Firm* — Smith IP Services, P.C.

(57) ABSTRACT

A method of determining rheological properties can include dispensing a fluid into a rheometer including a stator having at least one helical blade, measuring torque (T) due to relative rotation between the stator and a rotor of the rheometer at different rotational speeds (RPM's), calculating shear stress (SS) as follows: $SS=T^\beta/K$, and calculating volume averaged shear rate (VASR) as follows: $VASR=k1*RPM^\alpha$, where K, k1, $\alpha$ and $\beta$ are experimentally-derived coefficients. A method of mixing fluids and performing a rheological test on the admixed fluids can include dispensing a fluid into a rheometer, then dispensing another fluid into the rheometer, then mixing the fluids with at least one helical blade of the rheometer, and then measuring torque due to relative rotation between a stator and a rotor of the rheometer. A rotary rheometer can include a rotor, and a stator having at least one helical blade.

10 Claims, 24 Drawing Sheets

(56) References Cited

U.S. PATENT DOCUMENTS

| | | | |
|---|---|---|---|
| 8,347,693 B2* | 1/2013 | Pindiprolu et al. | 73/54.32 |
| 2003/0033859 A1* | 2/2003 | Schoeb et al. | 73/54.28 |
| 2003/0154772 A1* | 8/2003 | Jackson | 73/54.28 |
| 2003/0220742 A1 | 11/2003 | Niedermayr et al. | |
| 2004/0149019 A1* | 8/2004 | Johnson et al. | 73/54.28 |
| 2005/0132782 A1* | 6/2005 | Wallevik et al. | 73/54.28 |
| 2005/0138991 A1* | 6/2005 | Wallevik et al. | 73/54.02 |
| 2006/0207795 A1 | 9/2006 | Kinder et al. | |
| 2007/0168056 A1 | 7/2007 | Shayegi et al. | |
| 2007/0248454 A1 | 10/2007 | Davis et al. | |
| 2008/0105040 A1* | 5/2008 | Bivens et al. | 73/54.28 |
| 2008/0230220 A1 | 9/2008 | Morgan et al. | |
| 2010/0018294 A1* | 1/2010 | Tonmukayakul et al. | 73/54.28 |
| 2010/0071442 A1* | 3/2010 | Moon et al. | 73/54.28 |
| 2010/0181070 A1* | 7/2010 | Harris et al. | 166/280.1 |
| 2011/0024189 A1 | 2/2011 | Saeed et al. | |
| 2011/0061451 A1 | 3/2011 | Harris et al. | |
| 2011/0139464 A1 | 6/2011 | Henderson et al. | |
| 2011/0139506 A1 | 6/2011 | Lovorn et al. | |
| 2011/0139509 A1 | 6/2011 | Pool et al. | |
| 2011/0214882 A1 | 9/2011 | Santos | |
| 2011/0259612 A1 | 10/2011 | Lovorn et al. | |
| 2011/0290562 A1 | 12/2011 | Standifird et al. | |
| 2012/0048008 A1 | 3/2012 | Pindiprolu et al. | |
| 2012/0061087 A1 | 3/2012 | Iblings et al. | |
| 2012/0103610 A1 | 5/2012 | Turner et al. | |
| 2012/0186873 A1 | 7/2012 | Shayegi et al. | |

OTHER PUBLICATIONS

D.L. Lord, Helical Screw Rheometer: A New Tool for Stimulation Fluid Evaluation, SPE 18213, 1998.*

D.L. Lord, et al. Real-Time Fracturing Fluid Rheology Measurements With the Helical Screw Rheometer, SPE 19734, 1989.*

K L Mackey, R.G. Morgan and J.F. Steffe, "Effects of Shear-Thinning Behavior on Mixer Viscometry Techniques," submitted to Journal of Texture Studies, Michigan Agricultural Experiment Station, Journal Article No. 12280, pp. 1-17 (Apr. 1, 1987).*

"Section 8, Thickening Time Tests," pp. 22-28, American Petroleum Institute (believed to be published prior to Jan. 1999).*

T.A. Glen III and C.R. Daubert; "A Mixer Viscometry Approach for Blending Devices", Journal of Food Process Engineering, vol. 26, pp. 1-16, dated 2003, 16 pages.

Guillaume Delaplace et al.; "A New Expression of the Ks Factor for Helical Ribbon Agitators", The Canadian Journal of Chemical Engineering, vol. 78, pp. 393-394, dated Apr. 2000, 2 pages.

C. Salas-Bringas et al.; "A New On-Line Process Rheometer for Highly Viscous Food and Animal Feed Materials", Journal of Food Engineering, vol. 79, pp. 383-391, dated 2007, 9 pages.

Voula Vlachou et al.; "A New Tool for the Rheometric Study of Oil Well Cement Slurries Other Settling Suspensions", from the Cement and Concrete Research, vol. 30, pp. 1551-1557, dated 2000, 7 pages.

J. L. Valverde et al.; "An Improved Method for Determining Rheological Parameters of Suspension: Statistical Approach", from the Institution of Chemical Engineers, vol. 75, Part A, pp. 784-791, dated Nov. 1997, 8 pages.

Magdalena S. Tamura et al.; "Analysis of the Helical Screw Rheometer for Fluid Food", Journal of Food Process Engineering 16, pp. 93-126, dated 1993, 34 pages.

Wikipedia; "Archimedes' Screw", from the free online encyclopedia, last modified on Oct. 31, 2011, 4 pages.

K. P. Lai et al.; "Average Shear Rates in the Rapid Visco Analyser (RVA) Mixing System", Note from the American Association of Cereal Chemists, Inc. vol. 77, No. 6, pp. 714-716, dated 2000, 3 pages.

P. Guerin et al.; "Characterization of Helical Impellers by Circulation Times", The Canadian Journal of Chemical Engineering, vol. 62, pp. 301-309, dated Jun. 1984, 9 pages.

L. Zumalacarregui et al.; "Comparison Between Models Used in the Determination of the Rheological Parameters of Suspensions with Helical Screw Impeller", from the Institution of Chemical Engineers, vol. 78, Part A, pp. 419-424, dated Apr. 2000, 6 pages.

T. J. Akroyd et al.; "Continuous On-Line Rheological Measurements for Rapid Settling Slurries" article from Minerals Engineering, vol. 16, pp. 731-738, dated 2003, 8 pages.

T. J. Akroyd et al.; "Continuous Rheometry for Industrial Slurries", from the Experimental Thermal and Fluid Science, vol. 27, pp. 507-514, dated 2003, 8 pages.

T. J. Akroyd et al.; "Continuous Rheometry for Industrial Slurries", from the Department of Chemical Engineering at the 14th Australasian Fluid Mechanics Conference, dated Dec. 10-14, 2001, 4 pages.

J.P. Guillemin et al.; "development of a New Mixing Rheometer for Studying Rheological Behavior of Concentrated Energetic Suspensions", from the Journal of Non-Newtonian Fluid Mechanics, vol. 151, pp. 136-144, dated 2008, 9 pages.

K.L. Mackey et al.; "Effects of Shear-Thinning Behavior on Mixer Viscometry Techniques", from the Journal of Texture Studies, vol. 18, pp. 231-240, dated 1987, 10 pages.

TEMCO, Inc.; "Rheometer for Cement and Drilling/Fracturing Fluids Model RHEO-15", instruction manual, dated Aug. 13, 1996, 5 pages.

American Petroleum Institute; Rheo 15 Inroduction, received Jun. 21, 2008, 1 page.

Fann Instrument Company; "iX77 Rheometer", product information, dated 2007, 4 pages.

P.J. Cullen, et al.; "Rotational Rheometry using Complex Geometries", a review, dated Nov. 28, 2002, 20 pages.

Patrice Estelle, Christophe Lanos; "Shear Flow Curve in Mixing Systems—A Simplified Approach", Chemical Engineering Science vol. 63, 5887-5890, dated Aug. 22, 2008, 4 pages.

M. Elena Castell-Perez, et al.; "Simple Determination of Power Law Flow Curves using a Paddle Type Mixer Viscometer", research note, dated May 13, 1991, 14 pages.

Z. Kemblowski, et al.; "This Concept of a Rotational Rheometer with Helical Screw Impeller", Rheologica Acta vol. 27, pp. 82-91, dated 1988, 12 pages.

C. Salas-Bringas, et al.; "Time Variations and Calibrations of a Screw Type Process Rheometer", Applied Rheology vol. 20, Iddue 3, dated Dec. 16, 2009, 11 pages.

Pavla Novotna, et al.; "Use of Helical Ribbon Mixer for Measurements of Rheological Properties of Fruit Pulps", Czech J. Food Science vol. 19, No. 4, pp. 148-153, dated 2001, 6 pages.

Office Action issued Aug. 23, 2012 for U.S. Appl. No. 13/423,366, 19 pages.

Office Action issued Oct. 11, 2012 for U.S. Appl. No. 13/492,688, 17 pages.

Office Action issued Apr. 17, 2013 for U.S. Appl. No. 13/542,781, 10 pages.

Office Action issued Nov. 13, 2012 for Chinese Patent Application No. 200780049409.0, 5 pages.

English translation of Office Action issued Nov. 13, 2012 for Chinese Patent Application No. 200780049409.0, 5 pages.

Examination Report issued Sep. 28, 2012 for Australian Patent Application No. 2008365249, 3 pages.

S. Prakash, et al.; "Estimation and prediction of shear rate distribution as a model mixer", Journal of Food Engineering 44 (2000) 135-148, dated Nov. 11, 1999, 14 pages.

M. Castell-Perez, et al; "Evaluating Shear Rates for Power Law Fluids in Mixer Viscornetry", Journal of Texture Studies 21 (1990) 439-453, manuscript, dated Sep. 11, 1990, 14 pages.

I. Eriksson, et al.; "Evaluation of a Helical Ribbon Impeller as a Viscosity Measuring Device for Fluid Foods with Particles", Applied Rheology 12 (2002) 303-308, dated Nov./Dec. 2002, 6 pages.

M.S. Tamura, et al.; "Evaluation of the Helical Screw Rheometer as an On-line Viscometer", vol. 54, No. 2, 1989—Journal of Food Science 483-484, dated Jun. 19-22, 1988, 2 pages.

(56) References Cited

OTHER PUBLICATIONS

Jenni L. Briggs, et al.; "Mixer Viscometer Constant (k') for the Brookfield Small Sample Adapter and Flag Impeller", Journal of Texture Studies 27 (1996) 671-677, dated Aug. 30, 1996, 7 pages.

Alison P. Omura, et al; "Mixer Viscometry to Characterize Fluid Foods with Large Particulates", Journal of Food Process Engineering 26 (2003) 435-445, dated Mar. 17, 2003, 11 pages.

Institution of Chemical Engineers; "Mixing with Helical Ribbon Impellers: Effect of Highly Shear Thinning Behaviour and Impeller Geometry", Trans IChemE, vol. 75, Part A, dated Jan. 1997, 45 pages.

Magdalena S. Tamura, et al.; "Performance of the Helical Screw Rheometer for Fluid Food Suspensions", Journal of Food Science, vol. 58, No. 5, 1993, dated May 14, 1993, 6 pages.

Edmundo Brito-De La Fuente, et al.; "Process Viscometry of Complex Fluids and Suspensions with Helical Ribbon Agitators", That Canadian Journal of Chemical Engineering, vol. 76, Dated Jun. 29, 1998, 7 pages.

James F. Steffe; "Rhoelogiacl Methods in Food Process Engineering", second edition, referring to pp. 185-210, dated 1992, 1996, 428 pages.

Search Report and Written Opinion issued Feb. 12, 2014 for International Application PCT/US13/41121, 13 pages.

* cited by examiner

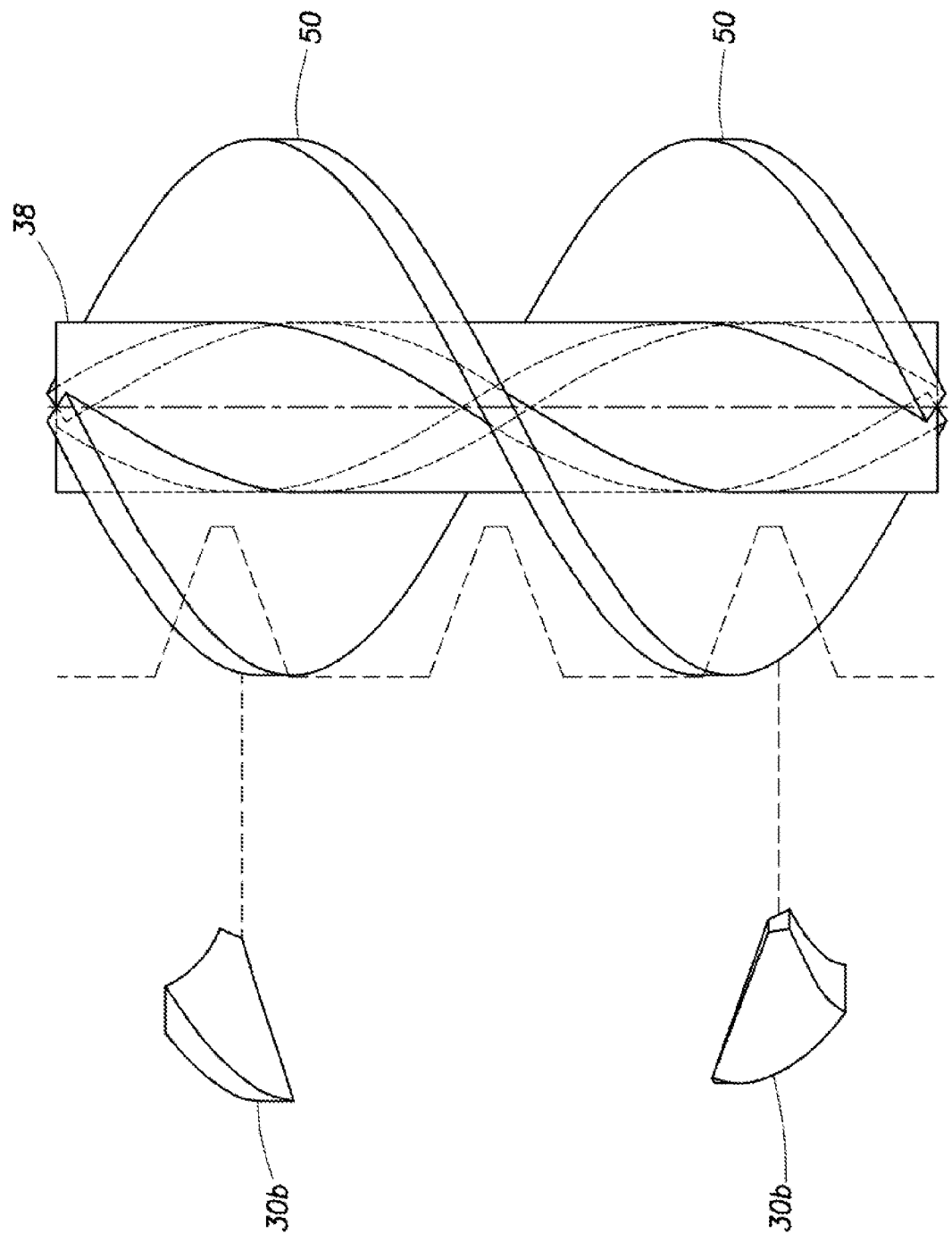

COMBINED RHEOMETER/MIXER HAVING HELICAL BLADES AND METHODS OF DETERMINING RHEOLOGICAL PROPERTIES OF FLUIDS

BACKGROUND

This disclosure relates generally to equipment utilized and operations performed in conjunction with rheological testing and, in an example described below, more particularly provides a combined rheometer and mixer having helical blades.

Various geometrical configurations have been used by rheologists to characterize the flow behavior of fluids under stress in rotational viscometry. The more common ones are bob/sleeve (couette) and impeller (mixer) geometries. Complex particle laden fluids used in the oil field pose unique challenges for rheological measurement in these geometries. These fluids, frequently, are a combination of light weight materials/weighting agents, clays, elastomers, polymers, resins, salts and cementitious materials in water or oil media. These fluids exhibit a high degree of non-Newtonian behavior, are sometimes thixotropic, have particle settling/phase separation issues when not sheared uniformly and sometimes are so thick/slippery to create coring and wall slip problems in the geometries where they are investigated.

In addition to maintaining the particles in suspension, some situations may also demand that two or more fluids be "homogenized in-situ" before carrying out the rheological measurements. The coefficients to convert torque-RPM data to rheograms are known to vary with the degree of shear thinning. A wide range of literature is available to corroborate this. Process engineers determine these coefficients for the set of fluids used in the plants on rheological instrumentation to deduce/monitor process behavior under varying shear rates, well in advance of a process being conducted.

However, all oil field fluids are different and a new "recipe" is formulated and mixed every time for subterranean operations. To understand the impact of these fluids on wellbore friction pressures, their solids carrying capability, their velocity profiles and the way they interact with other neighboring fluids, it is highly recommended to: a) carry out rheological experimentation in a geometry that will accurately probe the homogenous representative sample, and b) use correct conversion coefficients to deduce rheology from torque-RPM data. Unfortunately, prior rheometer geometries lead to errors due to: a) the fluid sample being probed is not a homogenous or representative sample, and/or b) measurement errors related to wall slip, inaccurate torque measurements (e.g., a stuck spring, etc.).

Compatibility tests are performed at times to determine whether certain fluids are compatible with each other. In order to ascertain compatibility of fluids related to cementing oil and gas wells, rheological characteristics of a base fluid are measured at downhole temperature and pressure, then a predetermined quantity of a second fluid at downhole temperature and pressure is added while mixing at a predetermined volume averaged shear rate. In subterranean well operations, examples of base and second fluids could comprise drilling fluid and fluid spacer, fluid spacer and cement slurry, drilling fluid and cement slurry, etc.

It would be beneficial to be able to provide an improved rheometer capable of supplying a predefined mixing step prior to accurately measuring rheological properties of fluids. The predefined mixing step could impart an integral shear history similar to that of fluid travel in a well with known characteristics. The improved rheometer could result from adapting an existing commercial rheometer with an improved rheometer geometry. Such an improved rheometer geometry would also be useful for rheological investigation in operations other than well operations.

SUMMARY

In the disclosure below, a rheometer (or rheometer geometry adaptable to an existing rheometer) and associated methods are provided which bring improvements to the art. One example is described below in which helical blades are used in a rheometer to promote efficient mixing of fluids and consistent shearing of the fluids between the blades. Another example is described below in which the fluids are separately dispensed into the rheometer, the fluids are mixed by the rheometer, and torque exerted by the rotating geometry in the rheometer is measured as an indication of the rheological properties and compatibility of the mixed fluids.

A method described below of determining rheological properties of a fluid can include:

a) dispensing the least one fluid into a rheometer including a stator having at least one helical blade;

b) measuring torque (T) due to relative rotation between the stator and a rotor of the rheometer at different rotational speeds (RPM's);

c) calculating shear stress (SS) as follows: $SS = T^\beta/K$; and d) calculating volume averaged shear rate (VASR) as follows: $VASR = k1 * RPM^\alpha$, where K, k1, $\alpha$ and $\beta$ are experimentally-derived coefficients.

In one aspect, this disclosure provides to the art a rheometer. The rheometer can include a stator and a rotor, with each of the stator and rotor comprising one or more helical blades.

In another aspect, a method of mixing fluids and performing a rheological test on the admixed fluids is described below. The method can include dispensing a fluid into a rheometer, then dispensing another fluid into the rheometer, then mixing the fluids with at least one helical blade of the rheometer, and then measuring torque due to relative rotation between a stator and a rotor of the rheometer.

In yet another aspect, a rotary rheometer is described below. The rotary rheometer can include a rotor, and a stator having at least one helical blade.

These and other features, advantages and benefits will become apparent to one of ordinary skill in the art upon careful consideration of the detailed description of representative examples below and the accompanying drawings, in which similar elements are indicated in the various figures using the same reference numbers.

BRIEF DESCRIPTION OF THE DRAWINGS

FIG. 6 is a representative side view of a blank and stator blades which may be used in the rheometer.

DETAILED DESCRIPTION

Figure 1:
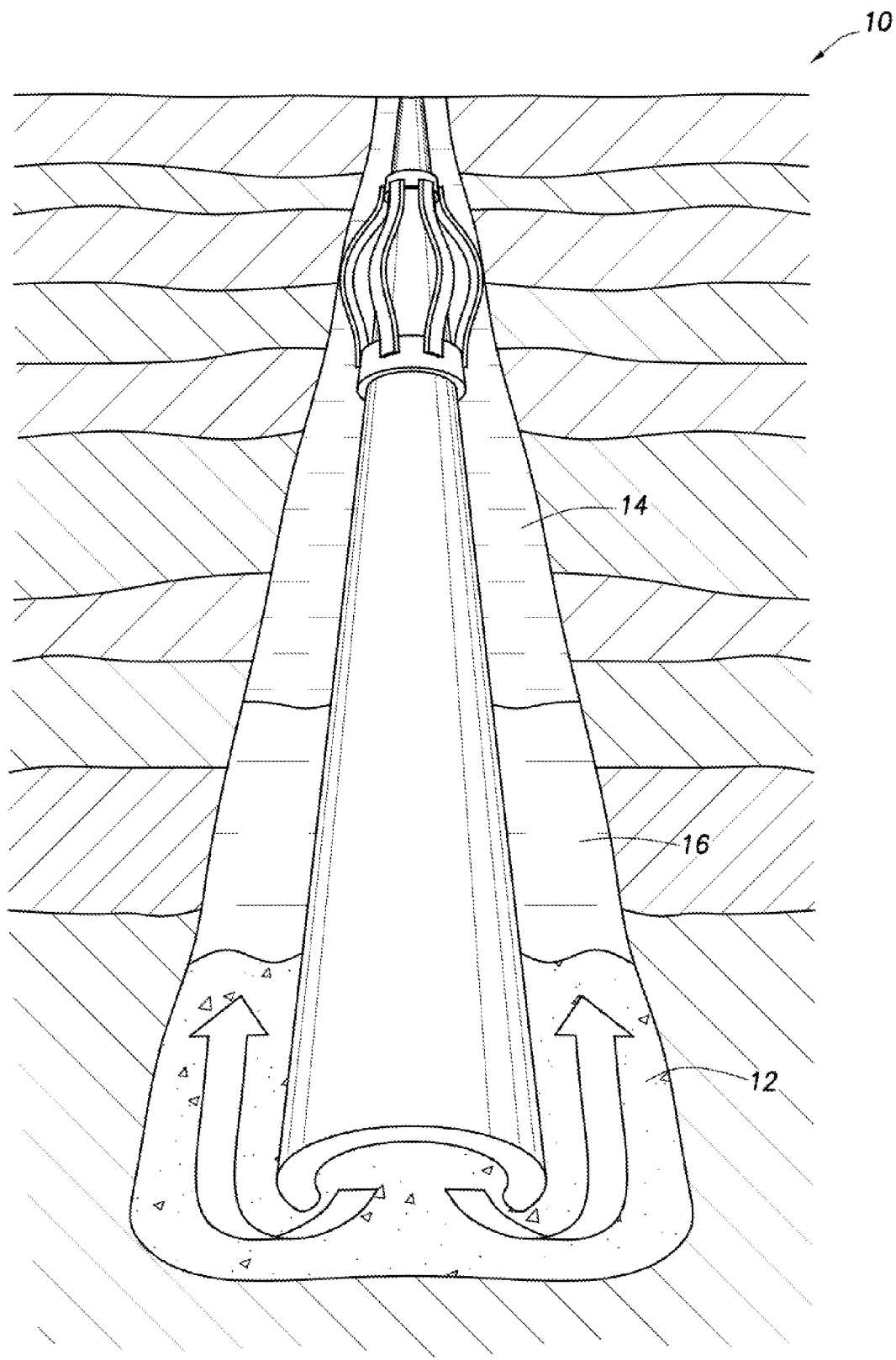
FIG. 1 is a representative partially cross-sectional view of a well system and associated method which can benefit from the principles of this disclosure.

Representatively illustrated in FIG. 1 is a well system 10 and associated method which can benefit from the principles of this disclosure. In the well system 10, various fluids are flowed through multiple flowpaths, and it is beneficial to be able to accurately characterize each of the fluids (and mixtures of the fluids), so that well operations can be most efficiently, safely, expeditiously, and effectively performed.

Note that the term "fluid" is used in this example to indicate a substance which flows at conditions experienced in a well (or other surrounding environment). Examples include (but are not limited to) cement 12 (prior to hardening), drilling fluid 14, a spacer 16, mixtures of spacer and drilling fluid, cement with drilling fluid and/or spacer, gases, etc. Any fluid or fluid mixture can be the subject of rheological investigation in keeping with the principles of this disclosure.

Rheological investigation of pure fluids itself is important. When fluids traverse down a pipe and up an annulus, they exert force on the walls of the pipe and the formation. Throughout the course of well operations, various fluids and their admixtures are subjected to various "Shear Rates". The Shear Rates they are subject to are a function of the geometry across which the fluids flow, and the local velocity at which they travel. Shear rates are "local" to the position of the fluid particle in the annulus. "Local Shear Rates" can be multiplied with "Apparent Viscosities at that shear rate" to get "Local Shear Stress" and hence velocity profile information.

For example, Local Shear rate at the wall can be multiplied with "Apparent Viscosity at that shear rate" to get Wall Shear Stress. Many times, local Shear rates can be averaged over the cross sectional area of flow to get "Volume Averaged" Shear Rates. Volume averaged shear rates will therefore vary as the fluids encounter annulus and pipe geometries of different dimensions, the fluids are subject to different pump rates when travelling thru the wellbore, etc.

The "Apparent Viscosities" for most well fluids are not constant with respect to Shear Rate. These fluids are called "Non-Newtonian—Shear Thinning Fluids" and are best described by a Generalized Herschel Bulkley Model (also known as GHB-4) or an industry standard Herschel Bulkley (HB) Model. For more information on these models, see Becker, T., et al., "Improved Rheology Model and Hydraulics Analysis for Tomorrow's Wellbore Fluid Applications," Society of Petroleum Engineers paper no. 82415 (2003).

Rheological testing can be carried out to determine the shear stress response of complex oil field fluids at various shear rates. Viscosity is not the same at all shear rates for complex oil field fluids.

Rheological investigation followed by correct calculations also provides information on many other field operational parameters including, but not limited to, pumping pressure, equivalent circulating density, pressure to break circulation and slurry mixing torque. It may also provide visco-elastic properties of the fluid and gel strength information.

In one example, the compatibility of certain fluids in the well system 10 might be the subject of inquiry. In one measure of compatibility, fluids are deemed compatible if an apparent viscosity of their admixture is between apparent viscosities of the individual fluids, at a given shear rate (where apparent viscosity is shear stress divided by shear rate). Therefore, it is desired to accurately measure the viscosity of the admixed fluids. Interfacial velocity profiles may also be determined with rheological information pertaining to the admixtures.

To enhance the accuracy of the viscosity measurement and replicate intermixing at wellbore conditions (e.g., enabling valid conclusions to be drawn and minimizing experimental error), it is preferred that the admixed fluids be well mixed at a predetermined volume average shear rate and for a predetermined mixing time, and the viscosity measurement be performed, using the same device. Rotary viscometers are known to those skilled in the art (such as Searle, Mooney-Couette, etc.). However, those viscometers have deficiencies with respect to combined mixing and viscosity measurement. Hereinafter, the term "homogenize" will refer to the process of applying a predetermined volume average shear rate to a fluid (or mixture of fluids) for a predetermined time.

At this point, it should be noted that the well system 10, the inquiry into the viscosity of the fluid mixture 16, the comparison to prior viscometers, etc. are described herein as examples of how the principles of this disclosure can be applied in practice. There are, of course, an unlimited number of other examples, and so it will be appreciated that the principles of this disclosure are not limited at all to the details of the well system 10 and associated methods described herein.

As another example, it is not necessary for any particular rheological proerty per se to be measured in keeping with the principles of this disclosure. Any rheological property of the investigated fluid (such as, elasticity, consistency, yield point (yield stress), shear stress, gel strength, degree of crosslinking, etc.) could be determined.

The measurements may be made by detecting electrical power draw by a motor, by detecting applied torque (e.g., detecting deflection of a spring, etc.), or by detecting any other parameter which provides an indication of a rheological property. One example of a rotary rheometer 20 which can embody the principles of this disclosure is representatively illustrated in FIG. 2.

In this example, the rheometer 20 includes a motor 22, a torque sensor 24, a rotor 26 and a stator 28. The motor 22 rotates the rotor 26 relative to the stator 28, and the torque sensor 24 measures torque due to shearing of the admixed fluids 12, 14. This is similar to a Searle-type rotary viscometer, which can incorporate the rheometer geometry described more fully below.

However, in other examples, other configurations of rheometers may be used, rheological properties of other fluids and other mixtures may be measured, etc. Therefore, it should be understood that the principles of this disclosure are not limited to the rheometer 20 described herein and depicted in the drawings.

Figure 3:
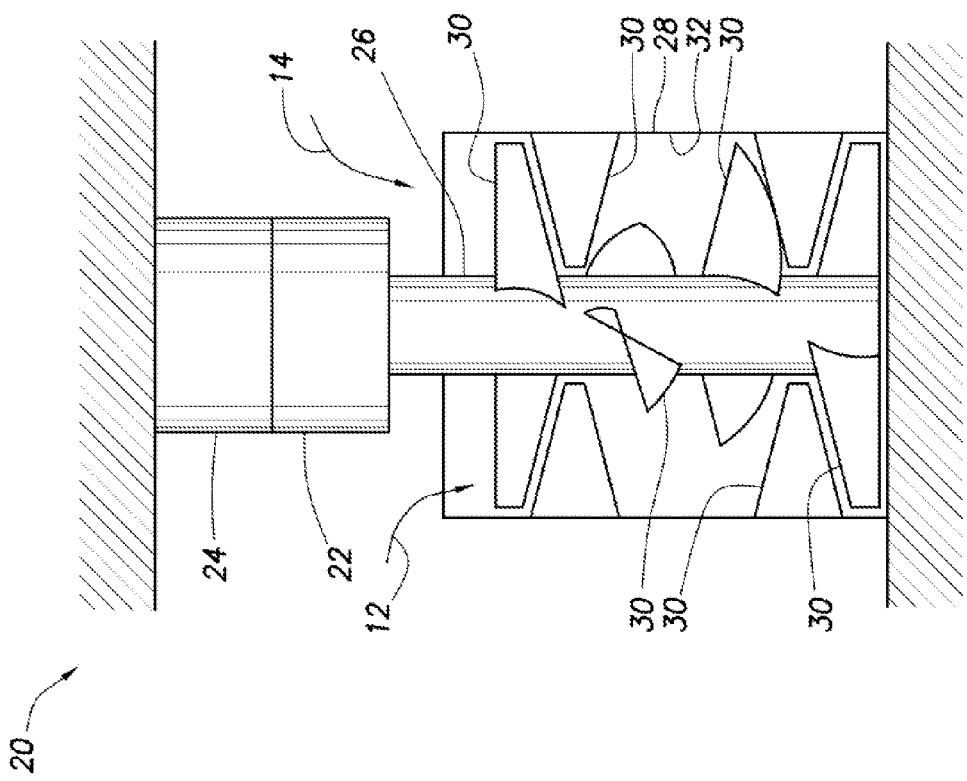
FIG. 3 is a representative partially cross-sectional view of another configuration of the rheometer.

One example of another configuration of the rheometer 20 is representatively illustrated in FIG. 3. In this example, the rotor 26 serves as a receptacle for the fluids 12, 14 and is rotated by the motor 22 positioned beneath the rotor. This is similar to a Couette-type rotary viscometer, which can incorporate the rheometer geometry described more fully below.

Figure 2:
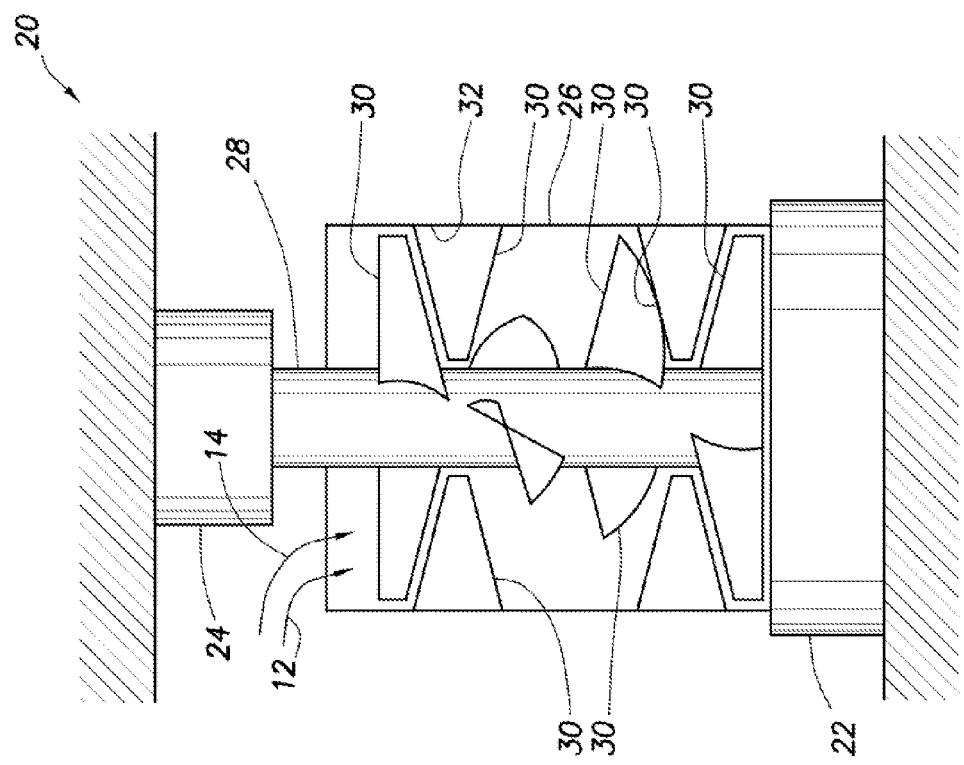
FIG. 2 is a representative partially cross-sectional view of a rotary rheometer which can embody principles of this disclosure.

In contrast, the FIG. 2 configuration has the stator 28 serving as a receptacle for the fluids 12, 14, with the rotor 26 being rotated by the motor 22 positioned above the rotor. This demonstrates that a variety of differently configured rheometers can incorporate the principles of this disclosure, and those principles are not limited to the details of any specific examples described herein.

One feature of the rheometer 20 as depicted in FIGS. 2 & 3 is that helical blades 30 are provided on the rotor 26 and on the stator 28. The helical blades 30 on the rotor 26 effectively homogenize the mixture of the fluids 12, 14, in part by ensuring that fluid at the bottom of the receptacle is urged upward toward the top of the receptacle.

Referring to FIG. 3, the helical blades 30 on the stator 28 are configured so that they intermesh with the blades on the rotor 26, and the fluid mixture is sheared in a space or gap between the blades. Preferably, the gap between the blades 30 is constant along the length of the gap, to thereby provide for consistent shearing of the fluid between the blades. Minimal variation in the gap between the blades 30 could be present, but preferably not to an extent which unacceptably degrades the resulting measurements.

In a method of performing rheological tests on the fluids 12, 14, one of the fluids is first dispensed into the receptacle, then another fluid is dispensed into the receptacle, and the rotor 26 is rotated relative to the stator 28 by the motor 22. The rotation of the rotor 26, in conjunction with the helical shapes of the blades 30 mixes and homogenizes the admixed fluids 12, 14. In other examples, the fluids 12, 14 could be mixed and/or homogenized prior to being dispensed into the receptacle.

Note that, in the FIG. 2 configuration, the blades 30 on the rotor 26 are axially spaced apart into separate flights, with the flights being separated by the blades on the stator 28. The blades 30 on the stator 28 are helically spaced apart on an inner generally cylindrical surface 32 of the stator. Of course, other configurations of elements in the rheometer 20 may be used, in keeping with the scope of this disclosure.

Preferably, the blades 30 on the stator 28 have the same shape and curvature as the blades on the rotor 26, so that the gap between the blades is uniformly consistent as one blade displaces past another, preventing interference between the blades, but providing for uniform intermeshing. One method of producing such complementarily shaped blades 30 is representatively illustrated in FIGS. 4-6, for the rheometer 20 of FIG. 2, but it should be understood that this is merely one example of how the blades could be produced, and other methods may be used in keeping with the scope of this disclosure.

For clarity, in the description below, the blades on the rotor 26 are indicated with reference number 30a, and the blades on the stator 28 are indicated with reference number 30b, it being understood that in other examples the specific blades could be on different ones of the rotor and stator, the blades could be differently configured, etc.

Figure 5:
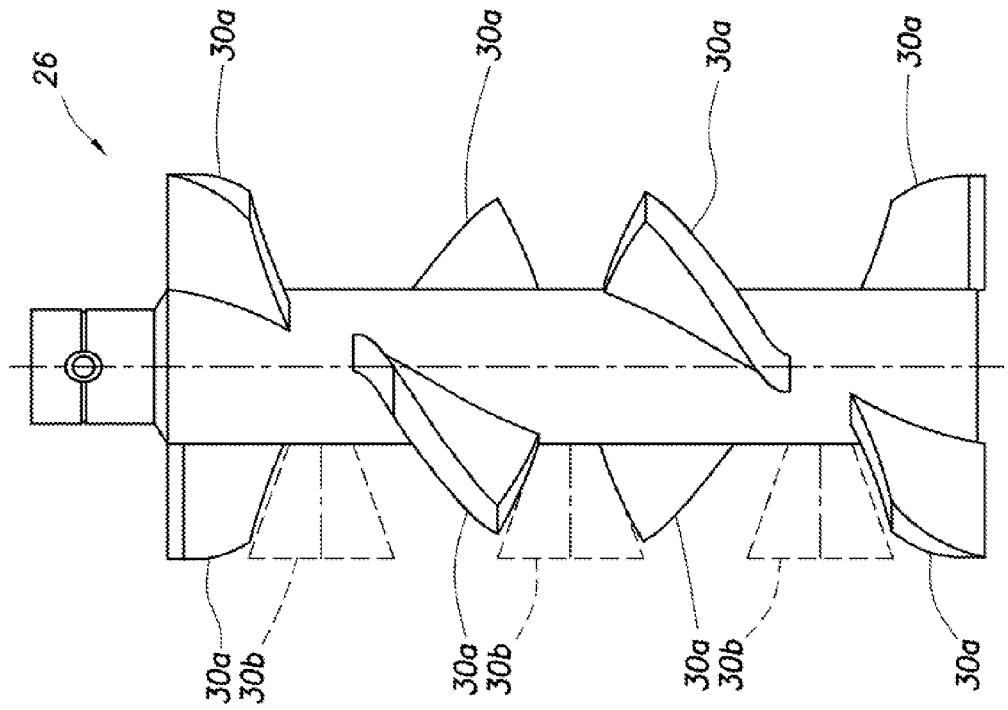
FIG. 5 is a representative side view of the rotor.
Figure 4:
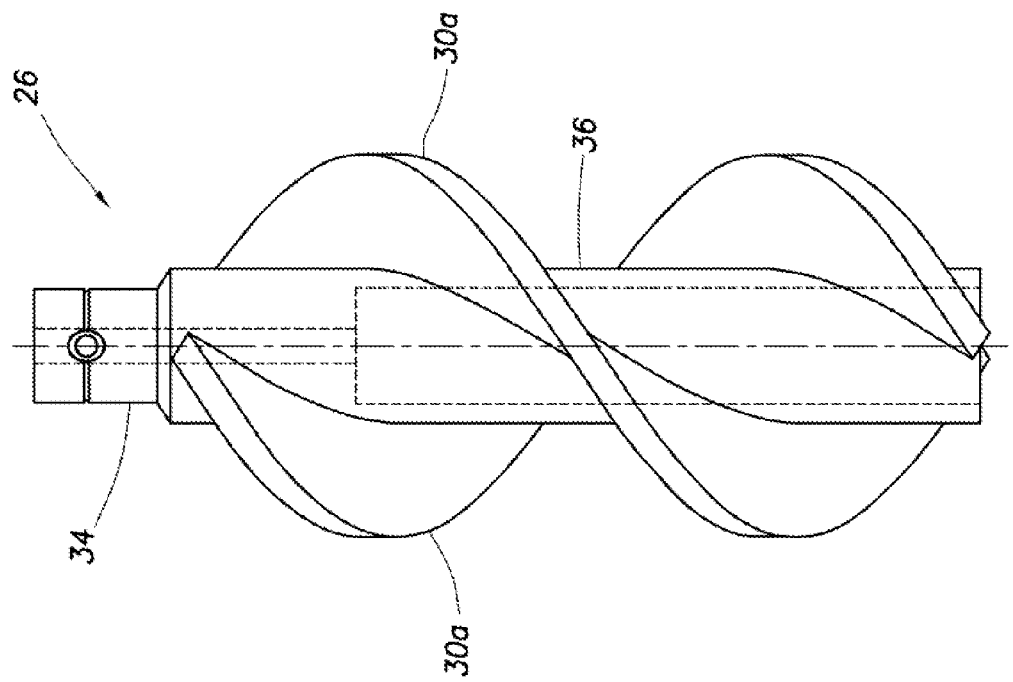
FIG. 4 is a representative side view of a blank for a rotor which may be used in the rheometer.

In the example of FIGS. 4-6, the rotor 26 begins as a cast or molded blank 34 having double helix blades 30a formed thereon. As depicted in FIG. 4, the blades 30a extend outwardly from a generally cylindrical surface 36 on the rotor 26. In other examples, the blades 30a could extend inwardly, the blades could extend from a non-cylindrical origin, different numbers of blades may be used, etc.

In FIG. 5, the rotor 26 is representatively illustrated after material has been removed from the blades 30a to accommodate the blades 30b on the stator 28. Note that, in this example, the chosen peripheral shape of the blades 30b is trapezoidal (in lateral projection), to provide a desired length of a desired gap between the blades 30a,b for shearing the fluids. In other examples, different shapes (e.g., rectangular, circular, polygonal, curved, combinations of shapes, etc.) of the blades 30b may be used.

As depicted in FIG. 5, the blades 30a are axially spaced apart along the rotor in four sets of flights. In other examples, more or fewer sets of flights may be used, as desired.

In FIG. 6, it may be seen that the blades 30b for the stator 28 are cut from another blank 38 having a double helix formed thereon, similar to the double helix blades 30a on the blank 34 of FIG. 4. In this technique, the trapezoidal shape is cut from the helixes 50 on the blank 38, thereby yielding multiple blades 30b which have substantially the same helical pitch (slope) and curvature as the blades 30a on the rotor 26.

Note that it is not necessary for the blank 38 to have a double helix formed thereon. Any number of helixes may be used in keeping with the scope of this disclosure. Indeed, the blades 30b could be formed by casting, molding, etc., without cutting them from a helix, if desired.

Figure 7:
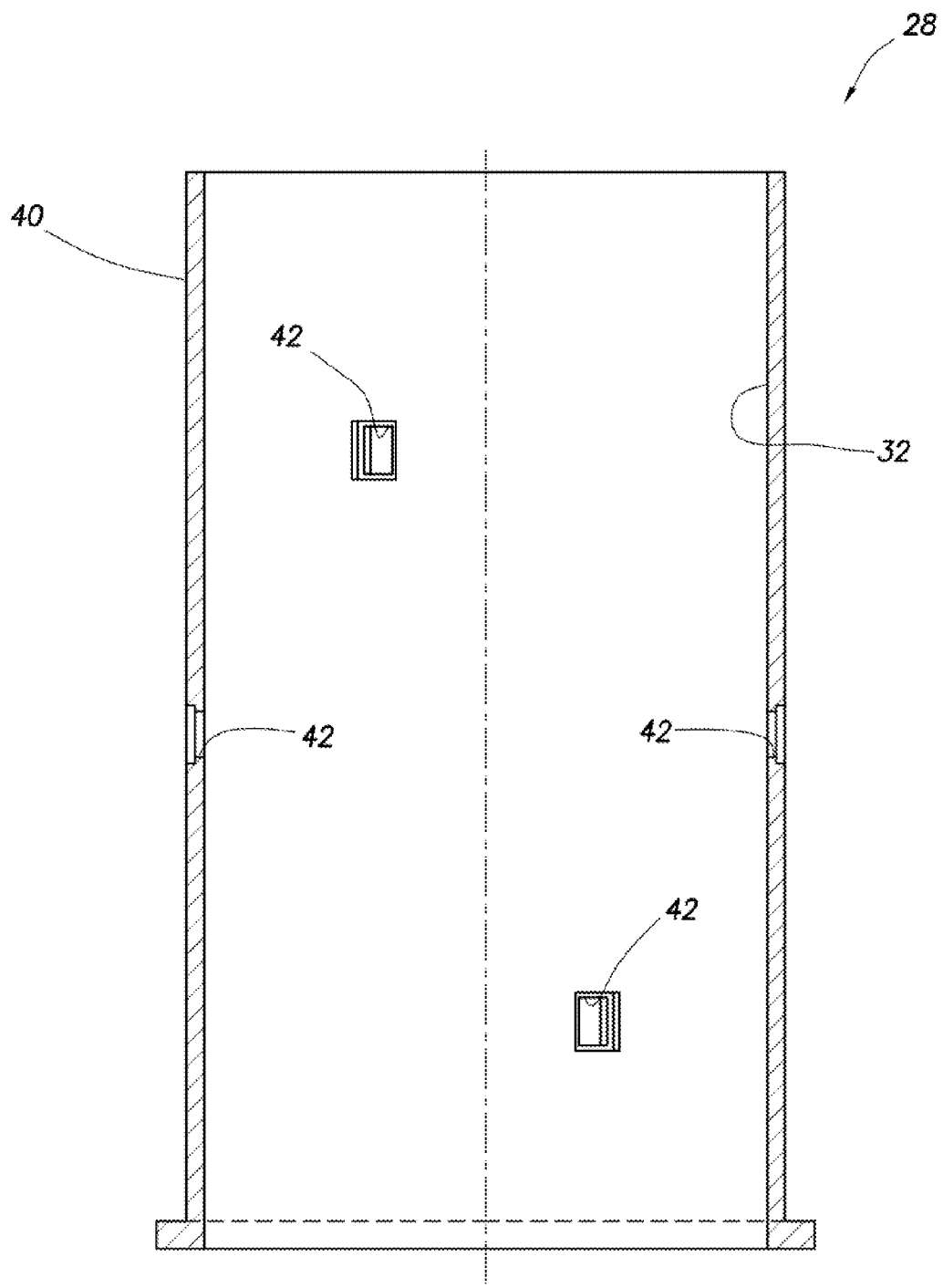
FIG. 7 is a representative cross-sectional view of a receptacle which may be used in the rheometer.

Referring additionally now to FIG. 7, a receptacle 40 of the stator 28 is representatively illustrated. The receptacle 40 is provided with a series of opposing recesses 42 which are helically spaced apart along the inner cylindrical surface 32 of the receptacle. The recesses 42 are used in this example to position the blades 30b on the stator 28. In other examples, the blades 30b could be otherwise positioned, configured or arranged.

Figure 8:
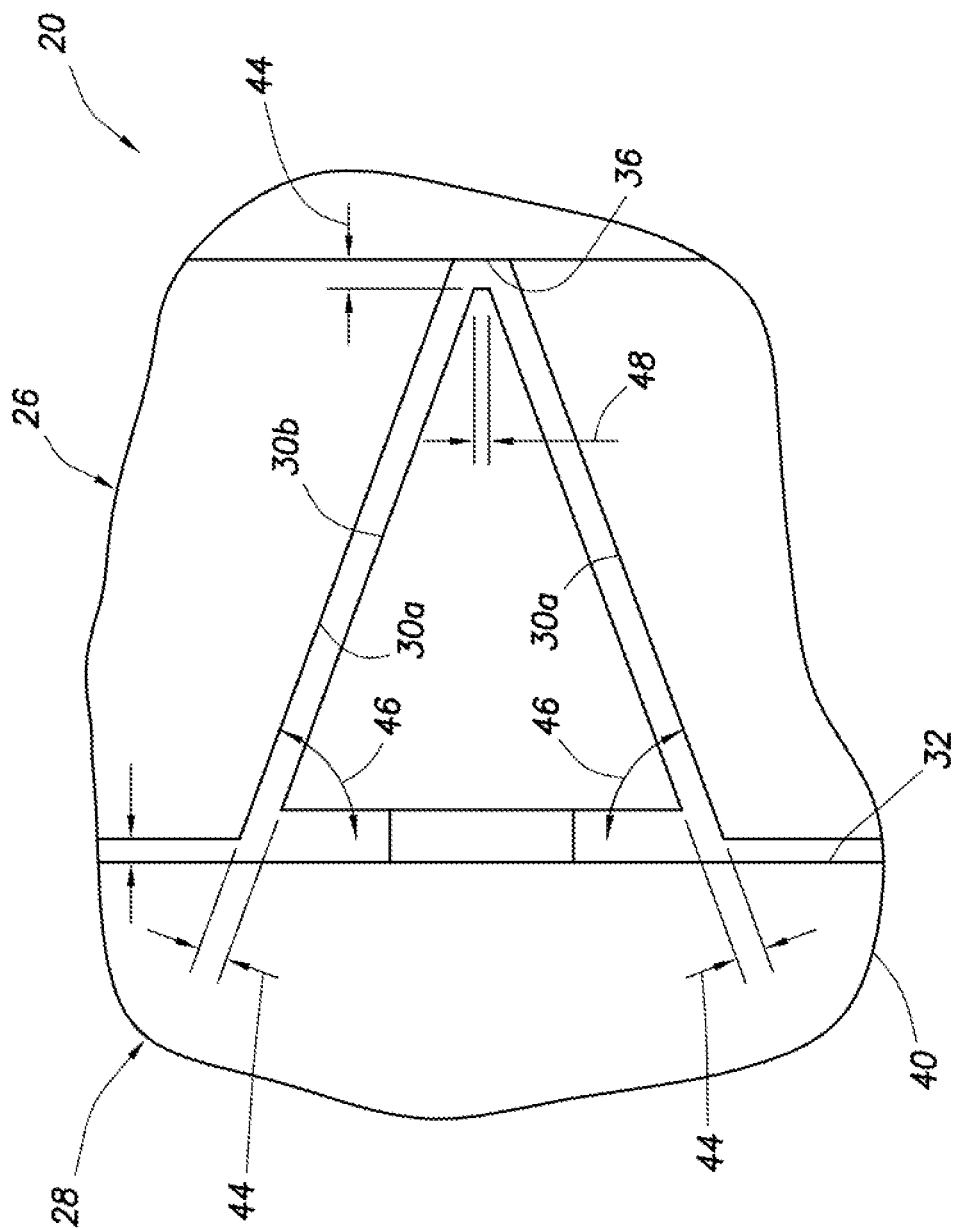
FIG. 8 is a representative side view of a consistent gap between rotor and stator blades in the rheometer.
Figure 9:
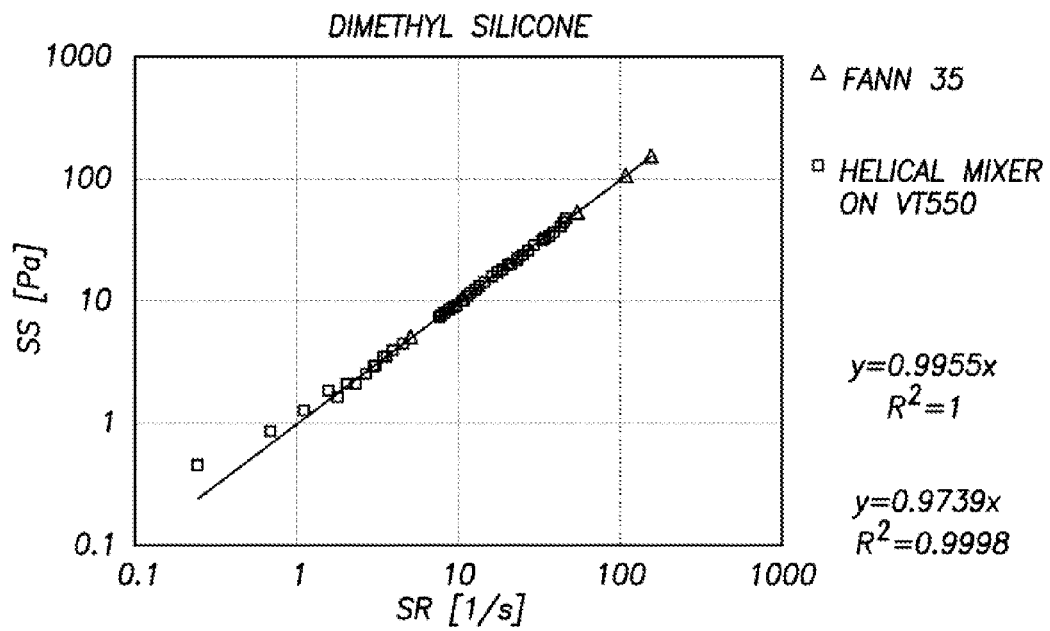
FIGS. 9-12 are plots of shear stress vs. shear rate for individual Newtonian fluids used for calibration with the matching slope method.
Figure 10:
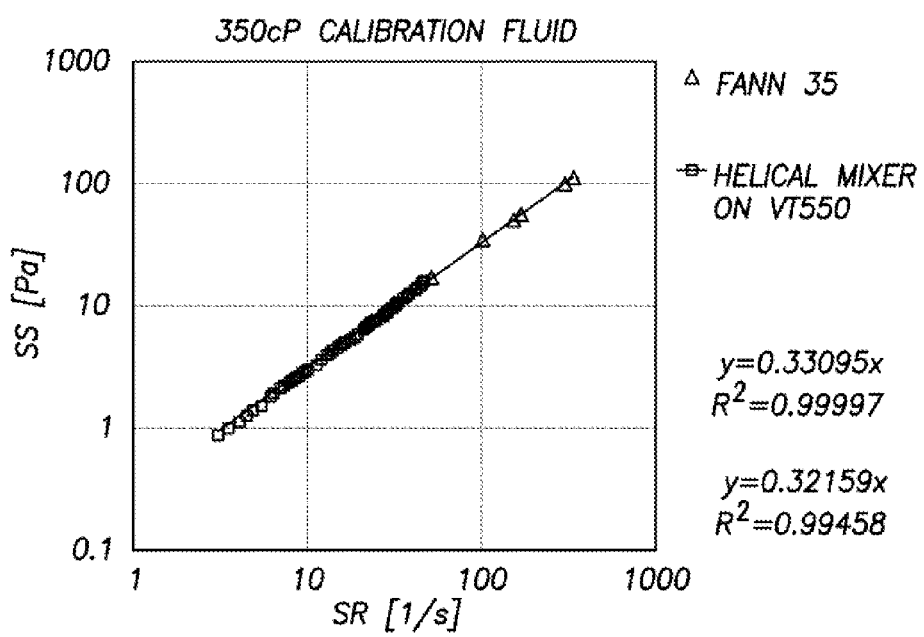
Figure 11:
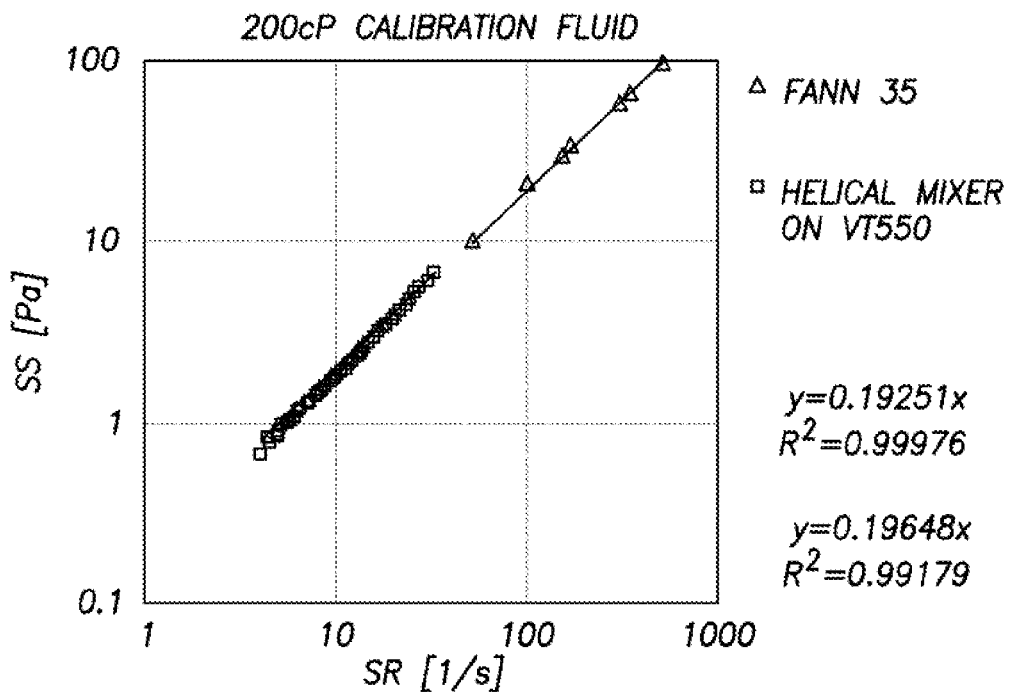
Figure 12:
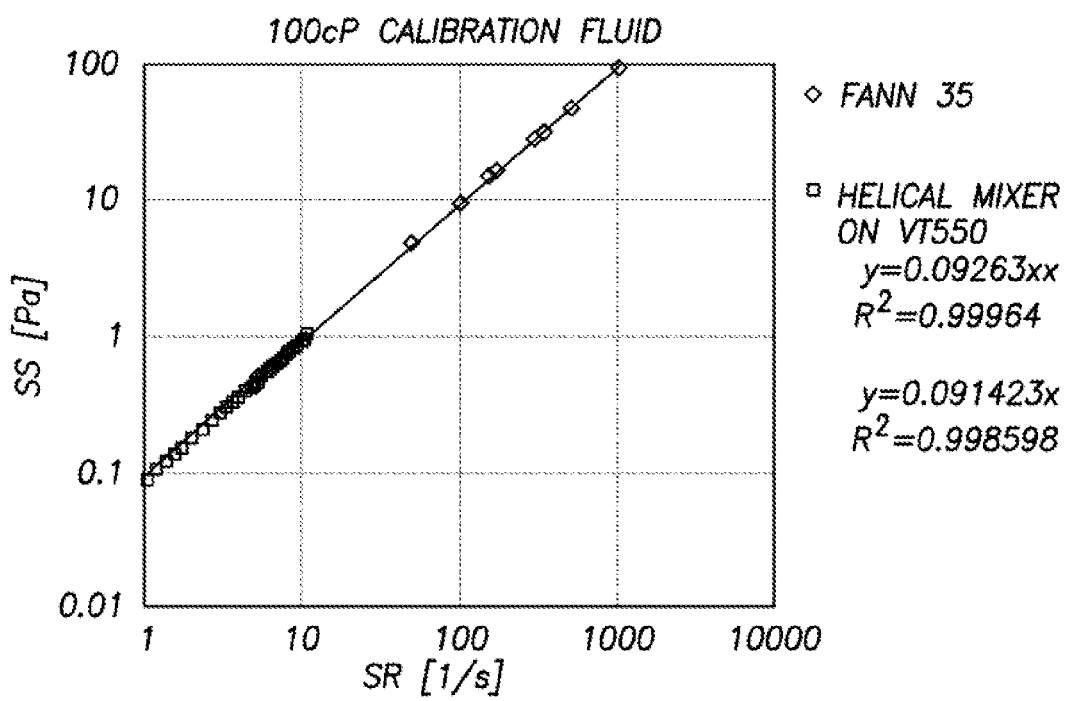

Referring additionally now to FIG. 8, an enlarged scale representative view of the blades 30a,b in the rheometer 20 is illustrated in lateral projection. The blades 30a,b are depicted in FIG. 8 as if "flattened" laterally, so that the blade 30b has its trapezoidal perimeter, and the blades 30a are axially separated by trapezoidal cutouts, as in the example of FIGS. 5 & 6. However, it will be appreciated that, in this example, the blades 30a,b are actually helical in shape.

Preferably, a gap 44 between the blades 30a,b is constant, or at least substantially consistent, so that the fluids are sheared between the blades consistently. However, some variation in the gap 44 may be permitted, if desired.

In a constructed example, a rheometer 20 had a consistent gap 44 of 0.150 in. (~3.8 mm) between the blades 30a,b and a base angle 46 of 70 degrees, with a tip width 48 on the blade 30b of 0.090 in. (~2.3 mm). Using this constructed example, the present inventors have developed a data analysis protocol and derived coefficients that are global and do not depend on the shear thinning index "n" of the fluid. These coefficients are, in turn, used to convert torque-RPM data into stress-strain data (rheology data) irrespective of the shear thinning index of the fluid, and provide for a means to derive rheograms.

In contrast, prior mathematical models for converting torque-RPM data generated from mixer geometries to meaningful rheograms incorporate coefficients that are dependent on the shear thinning index of the fluid. Shear thinning index is itself a rheological parameter that is derived by model fitting on rheological data. Shear thinning index is commonly referred to as "n" in HB/GHB models and is a degree of the shear thinning behavior of a fluid.

Rheology measurement for complex fluids is an implicit problem with helical geometries. The present inventors' protocol enables this to be done explicitly by deriving the correct coefficients, and by proving experimental comparisons.

Using commercial software, computational fluid dynamics (CFD) simulations were carried out to understand the flow profiles in this geometry. Additionally, constants k1 and K that are required to convert torque-RPM data into Shear Stress-Shear Rate respectively were determined.

Initial simulations showed the need to increase the rotor diameter in order the increase the volumetric average shear rates at a given RPM to the desired limit. The geometry was re-designed, and simulations were repeated for a Newtonian and Non Newtonian fluid at two different RPMs to recalculate k1 and K.

The helical mixer assembly was then manufactured and connected to a commercially available rheometer, Haake VT550, to measure torque-RPM data for a wide array of fluids. Data was collected for various Newtonian fluids, viscosity ranging from 10 cP to 1000 cP. Power number vs. impeller Reynolds number was plotted to derive a functional relationship between these quantities in the laminar and turbulent regimes.

It was observed that the onset of transitional flow occurs around a Reynolds number (with respect to the rotor) of 200. From this experimental data, values of k1 and K were estimated which matched well with the values obtained from the CFD simulations. Rheograms that were plotted using these values of k1 and K are shown in FIGS. 9-12.

Torque-RPM data was then generated for various non-Newtonian fluids, e.g., linear gels, visco-elastic fluids, Power law fluids, oil and water based muds, spacers and different types of cement slurries that are used to service wellbores. The same fluids were also investigated on a standard bob and sleeve geometry, as well as a triangular impeller geometry.

Mathematical modeling was carried out on these data to fit a four parameter Generalized Herschel Bulkley model to characterize complex fluids. A unified algorithm and data analysis protocol has been developed to convert the torque—RPM data into rheograms for all the said fluids using coefficients that do not change with respect to shear thinning index. These coefficients are global and remain constant for all fluids whilst maintaining least error between the experimental data and the mathematical models that were fit on both cylindrical as well as helical mixer geometries.

Visual experimentation was carried out with a tracer at the bottom of the rheometer 20. Upon rotating the rotor, the tracer fluid mixes homogenously along the complete length of the fluid column. Thick bread flour dough was also loaded to the bottom of the mixer and extrusion and conveyance from bottom to top was clearly observed along with flow transfer from one side to the other at the top.

Rheological incompatibility was clearly observed on fluid mixtures in the rheometer 20 giving rise to elevated rheograms as compared to the base fluids themselves. Moreover, the degree of compatibility between the base fluids could also be clearly captured at various volume fractions by generating accurate rheograms that appeared in between the rheograms of the pure fluids.

At the same rotational speed for the triangular mixer, the rheometer 20 generates only half of the shear rate, and is thereby able to measure the yield point of the fluids more accurately. Shaving foam and tomato ketchup were used for this purpose and it has been verified that the yield point values match with the data obtained on commercial viscometers using both mathematical modeling as well as the decay method. It may be appreciated that yield point measurement may not be carried out accurately on commercial viscometers for complex fluids like cement slurries owing to wall slip/coring/settling problems.

In summary, the helical mixer geometry can accurately characterize rheological behavior of particle laden fluids exhibiting varying degrees of shear thinning behavior using a unified data analysis protocol. Gel Strength measurements may also be carried out more accurately as compared to prior art techniques. In situ homogenization can be efficiently carried out in this device, thereby enabling accurate "mix while measure" techniques for particle laden slurries and their admixtures.

The most common rheology measurement technique used in the oil field is the Couette-type viscometry exemplified by the Fann 35 viscometer. An outer sleeve spins at a designated RPM and an inner bob deflects to a corresponding degree when a fluid is sheared in an annulus between the bob and the sleeve. A viscometric flow is established in such a device. Torque on the bob is measured, and based on the area of contact, a shear stress is calculated.

Equations are available to calculate the shear stress at the bob, depending on the rheological model that the fluid follows (e.g., see standard references in the field of rheology, such as, page 161 in section 3.2.1 of "Rheological Methods in Food Process Engineering" by James E. Steffe). Further to this, it may be appreciated that the problem of rheological model determination by measuring torque and RPM data on viscometric devices is iterative.

It is understood by those skilled in the art that complex fluids are present in wells. These fluids do not necessarily follow Newtonian behavior and their rheological properties may also change with respect to operating conditions in a wellbore.

Since the fluids are also most of the time particle laden, the Couette viscometry techniques may not yield proper rheological information. More so, polymer systems present in the fluids and the presence of a finite yield point may also violate the "no-slip" boundary condition that is a necessary assumption to predict rheology correctly on such devices.

In compatibility measurements, two fluids may be homogenized with various compositional ratios, and their rheological experimentation may be carried out at wellbore conditions without the need of using a separate motor for homogenizing and conditioning. Compatibility measurements give us an insight into the physical and/or chemical reactions happening between these fluids at their interfaces, and also using this data we can accurately predict the interfacial velocity profiles in the wellbore. Therefore, in addition to all the challenges faced with conventional Couette devices and already existing mixing devices (that may keep the particles in the slurry in suspension and have shear gaps not interfering with rheology measurement), a new challenge for doing rheology of mixtures is to homogenize and "mix while we measure."

The present inventors have observed that in this attempt to homogenize the fluids, the rheometer 20 can possibly induce turbulence and create experimental errors when proper care is not taken to eliminate the turbulent data points during rheogram construction.

For example, if we plot torque on the Y axis and RPM on the X axis for a Newtonian fluid tested on this device, a straight line should result, as long as viscometric flow is maintained in the shear gaps. Some local pockets of high shear mixing can be created but, overall, as long as an average viscometric flow is maintained, we can conclusively say that the volume averaged flow regime is laminar. The onset of turbulence can be clearly seen by a deviation from the straight line behavior and a change in the slope at higher speeds.

For the purpose of this disclosure "Shear Stress" pertains to the laminar flow regime alone, therefore all data in the turbulent regime is eliminated for the data analysis.

In helical mixers like the examples described above, there may be a possibility of a normal stress component and vortices contributing to torque and, therefore, only the data in the linear regime of torque vs. RPM should be used to infer rheograms.

The following approach was used to generate and validate the design:

1. Computation fluid modeling was used to determine the geometry and estimate geometry constants. The constants are Torque/Shear Stress Ratio which will be indicated as "K" and VASR[sec$^{-1}$]/RPM (volume averaged shear rate/revolutions per minute) ratio which will be indicated as k1. Initial design dictated that k1 was close to 0.08 as against the mixer device (FYSA) commercialized at the time of designing this rotor that had a k1 close to 0.25. The OD of the vanes in the rotor was therefore increased and k1 was increased to 0.158. However, this increase in shear rate was a tradeoff of early onset of turbulence as compared to the first design.

2. Computational Fluid Dynamics simulations of 500 cP fluid at 100 RPM gave a torque of 4.592 mN-m on the rotor. The average Shear rate was computed to be 15.805 sec$^{-1}$. Therefore, a shear stress can be calculated as 0.5 Pa*15.805 sec$^{-1}$=7.9025 Pa. Therefore, T/SS=K=4.592E-3/7.9025=5.8108 E-4. Similarly, T/SS Ratio was calculated as 5.767E-4 for the 500 cP fluid at 6 RPM.

These coefficients k1 and K are validated against experimental findings. In experimental validation, the first set of data was generated for Newtonian fluids.

Newtonian fluids allow the linear regime to be appropriately estimated, to avoid turbulent data points because Torque speed response in the laminar regime will always be linear for Newtonian Fluids. Moreover, for the first set of experiments, it is not desired to have a finite yield point to be present in the fluid because this will help the experimentalists to say with confidence that friction related errors are not present in these rheological experiments.

The process may be summarized as follows:

1. For power law fluids, we started off with matching the slopes of LOG(SS) vs. LOG(SR) on both the Fann 35 and the rheometer 20. It was observed that the value k was slightly changing with respect to changing shear thinning index of standard Power Law fluids. This was also reported by other researchers in literature previously.

2. Rheological fingerprint is typically determined iteratively for the shear thinning fluids. Here the variation of coefficients to convert RPM to SR is a function of the shear thinning index of the fluid.

3. But, in well operations, many different fluid formulations may be mixed, unlike the process industry where they deal with a known set of fluids, and very well know what their rheological fingerprint is. Only by generating rheograms can we calculate 'n'. So, we want to fit a functional relationship between RPM and SR, torque and SS, which is independent of 'n'.

4. We appreciated that the functional relationship's coefficient alpha was changing on a log-log analysis between SR and SS only for "highly" shear thinning fluids, and such highly shear thinning fluids are rarely encountered in wells.

5. We went ahead to analyze particle laden fluids also. Moreover, doing a plot of log(SS) and log(SR) would not help us to determine: a) coefficients exactly, b) yield point, if present, or c) different coefficient values for different fluids.

It is established in the literature that, in most commercial mixers, the relationship between Power number and Reynolds number is $$N_{Po} = A^* (N_{Re,I})^B \quad (14)$$

For Laminar flow, B=−1
For Transitional flow, −1<B<0
For turbulent flow, B=0

For Newtonian fluids, the following steps were followed to determine A and B:

1. RPM is converted into radian/s (Ω)
2. Power number is calculated using formula, $$N_{Po} = (T^*\Omega)/(\Omega^{3*}d^{5*}\rho) \quad (12)$$

3. Reynolds number with respect to impeller speed is calculated using the following formula, $$N_{Re,I} = (\Omega^* d^{2*}\rho)/\mu \quad (13)$$

Viscosity of Newtonian fluids is measured on a Brookfield viscometer.

4. Consolidated Log($N_{Po}$) vs. Log($N_{Re,I}$) is plotted.
5. When Log($N_{Po}$) vs. Log($N_{Re,I}$) is plotted, in the laminar regime, this plot should be a straight line with B as the slope and Log(A) as the intercept.

Since Log(A)=Intercept, therefore $$A = (10)^{Intercept} \quad (15)$$

$$B = \text{Slope} \quad (16)$$

Figure 13:
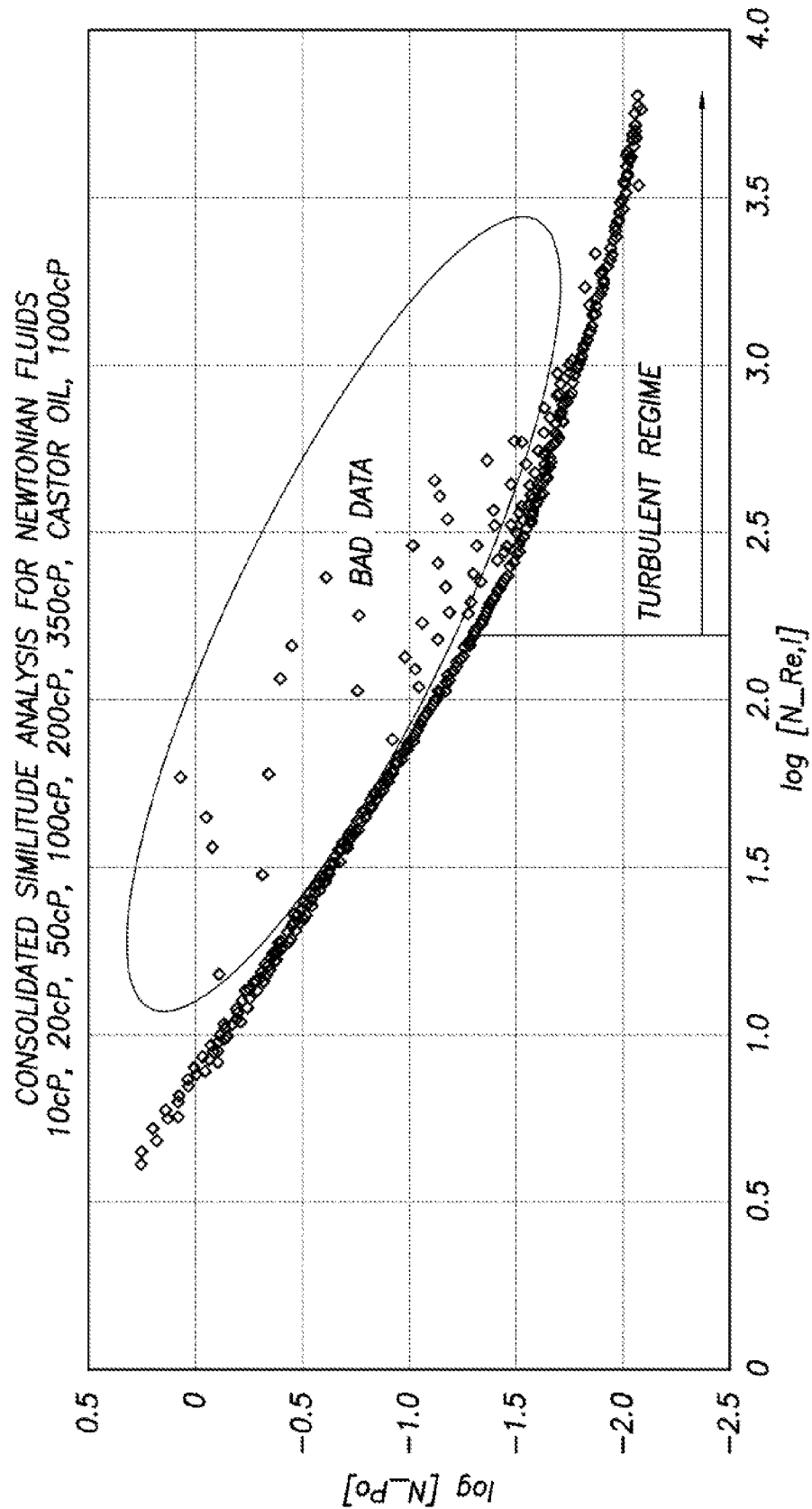
FIGS. 13 & 14 are plots of $\log(N_{Po})$ vs. $\log(N_{Re,I})$ after carrying out a combined similitude analysis with eight different Newtonian fluids.
Figure 14:
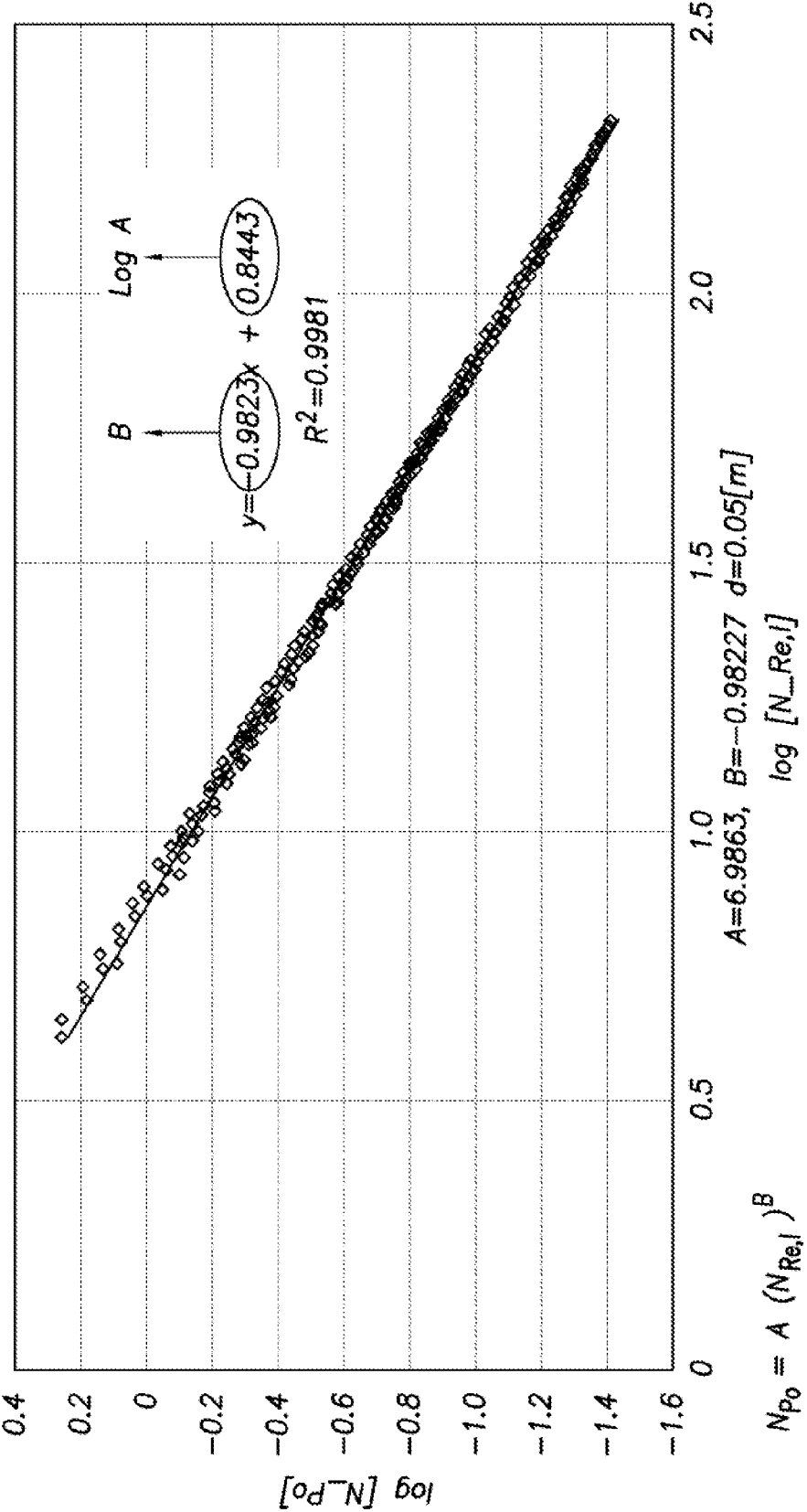
Figure 15:
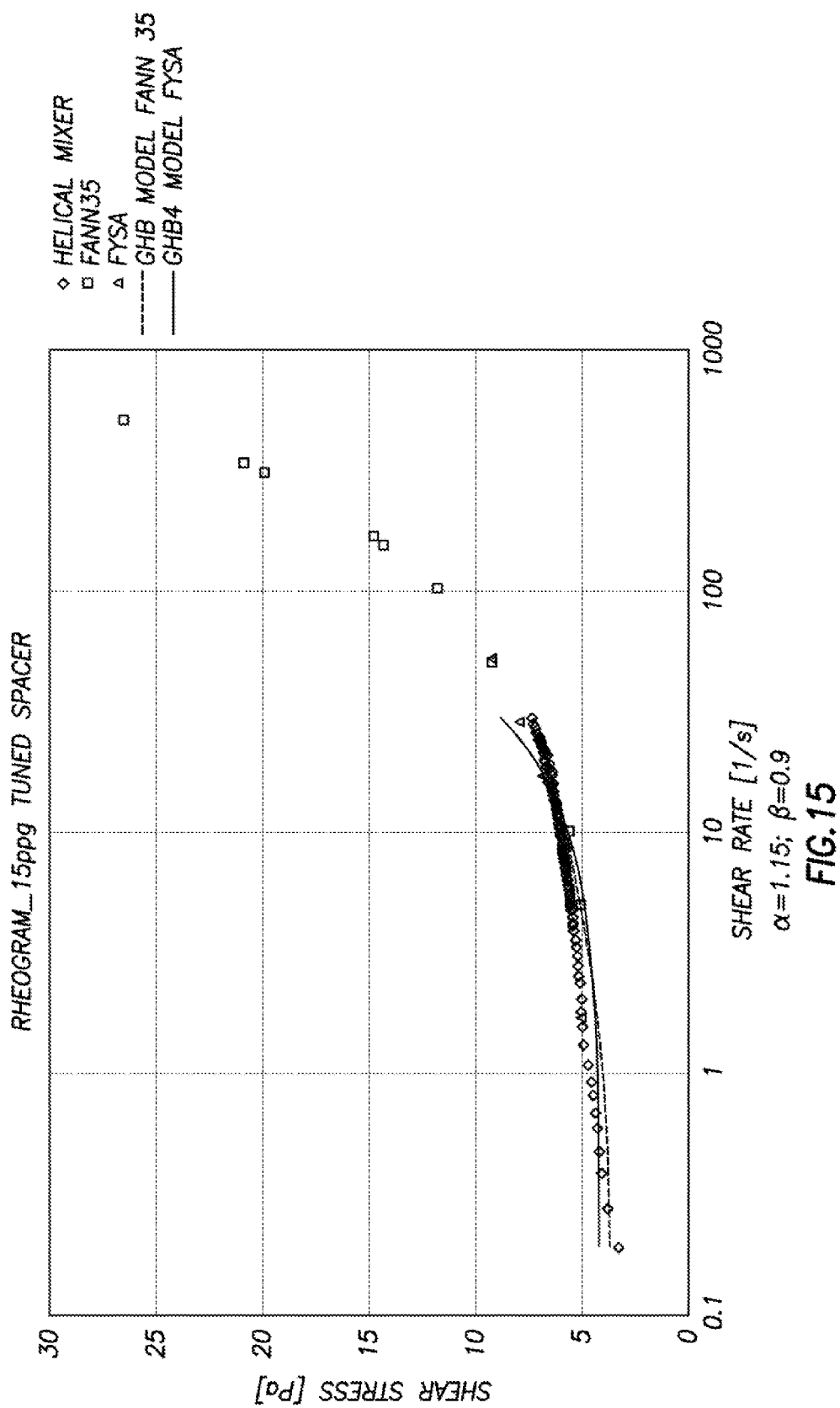
FIGS. 15-23 are rheograms of experimental data for various non-Newtonian fluids as investigated on a standard Couette (Fann 35), a triangular vane (FYSA, marketed by and proprietary to Halliburton Energy Services) and the respective GHB 4 models fitted on the Fann 35 and FYSA.
Figure 16:
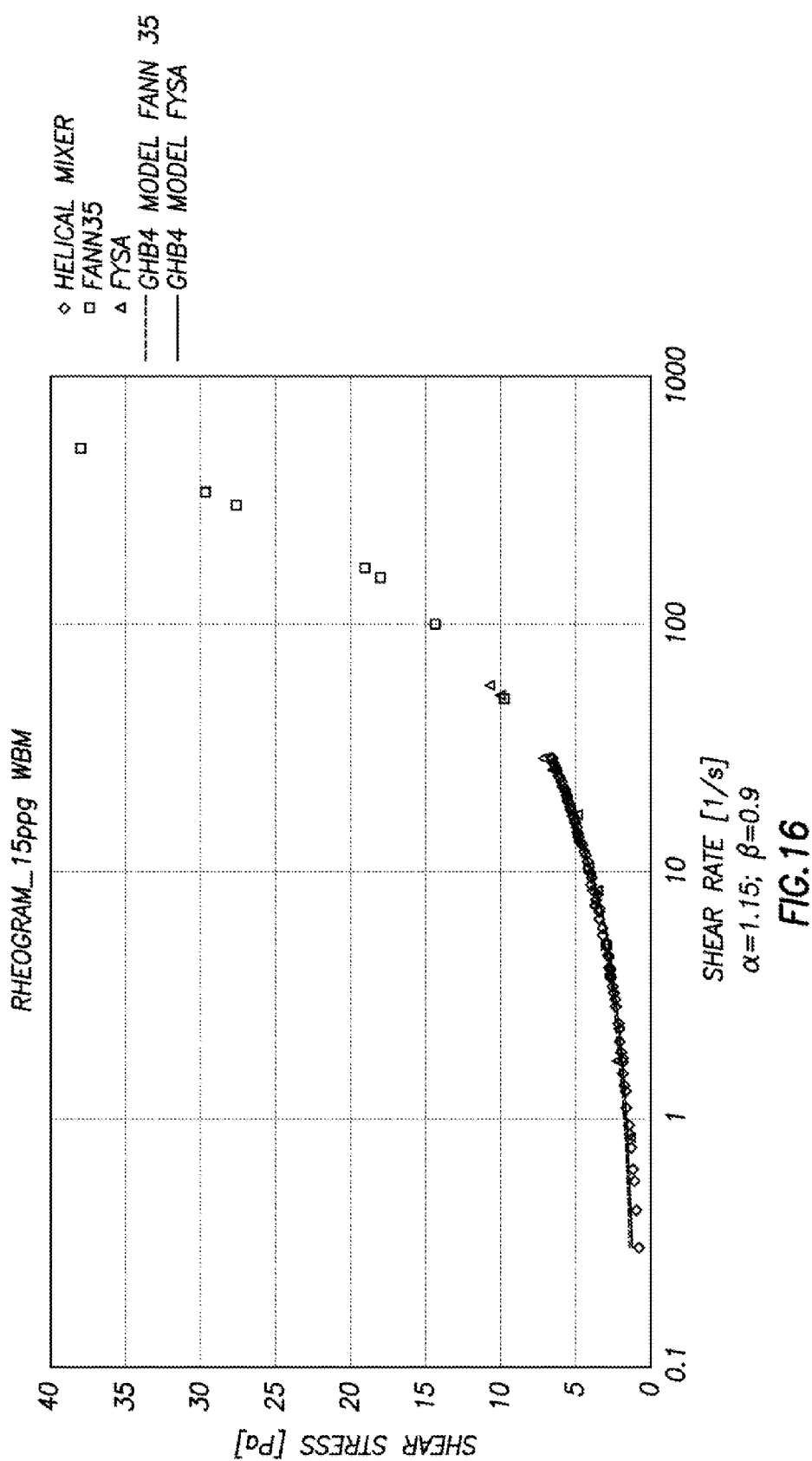
Figure 17:
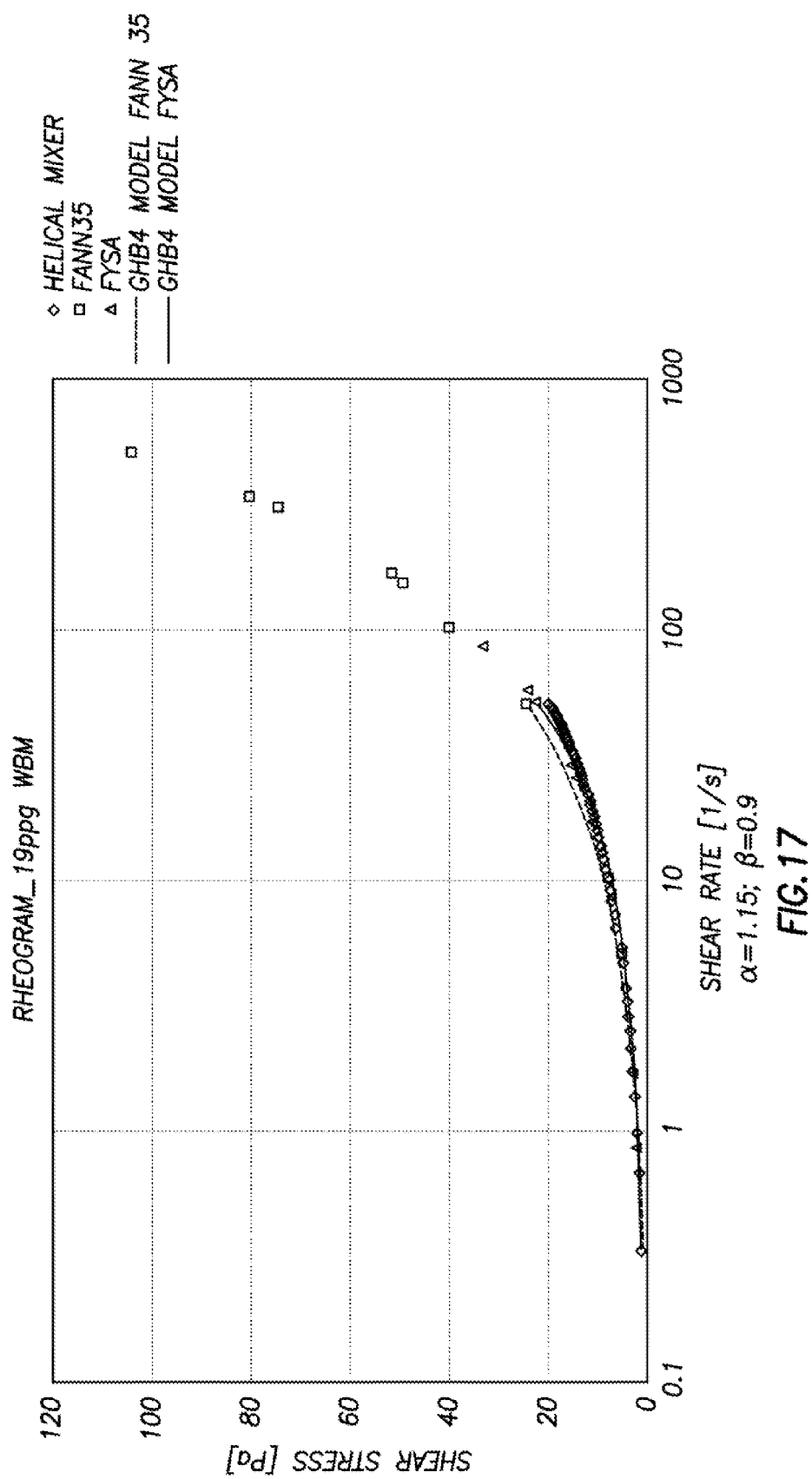
Figure 18:
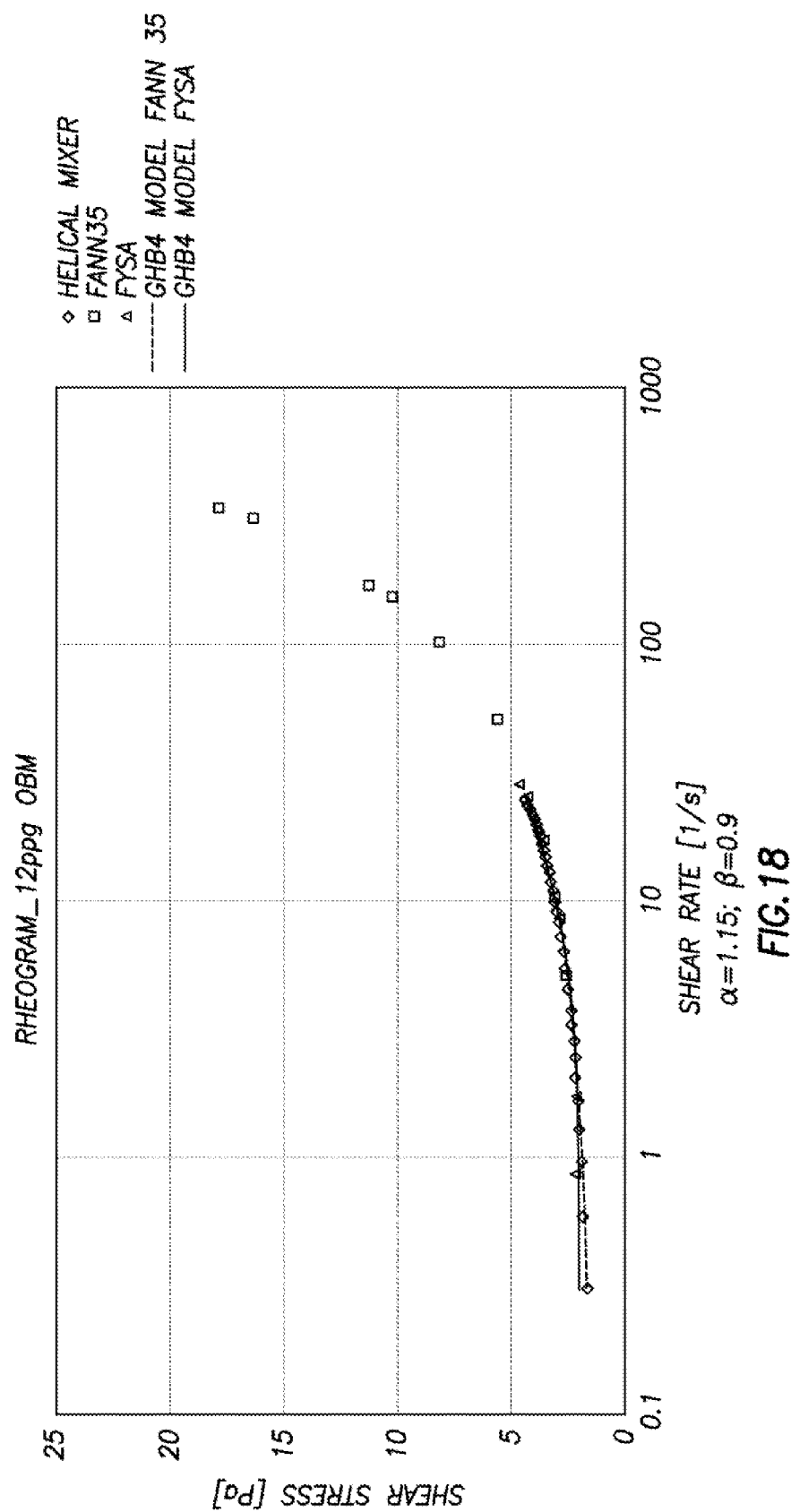
Figure 19:
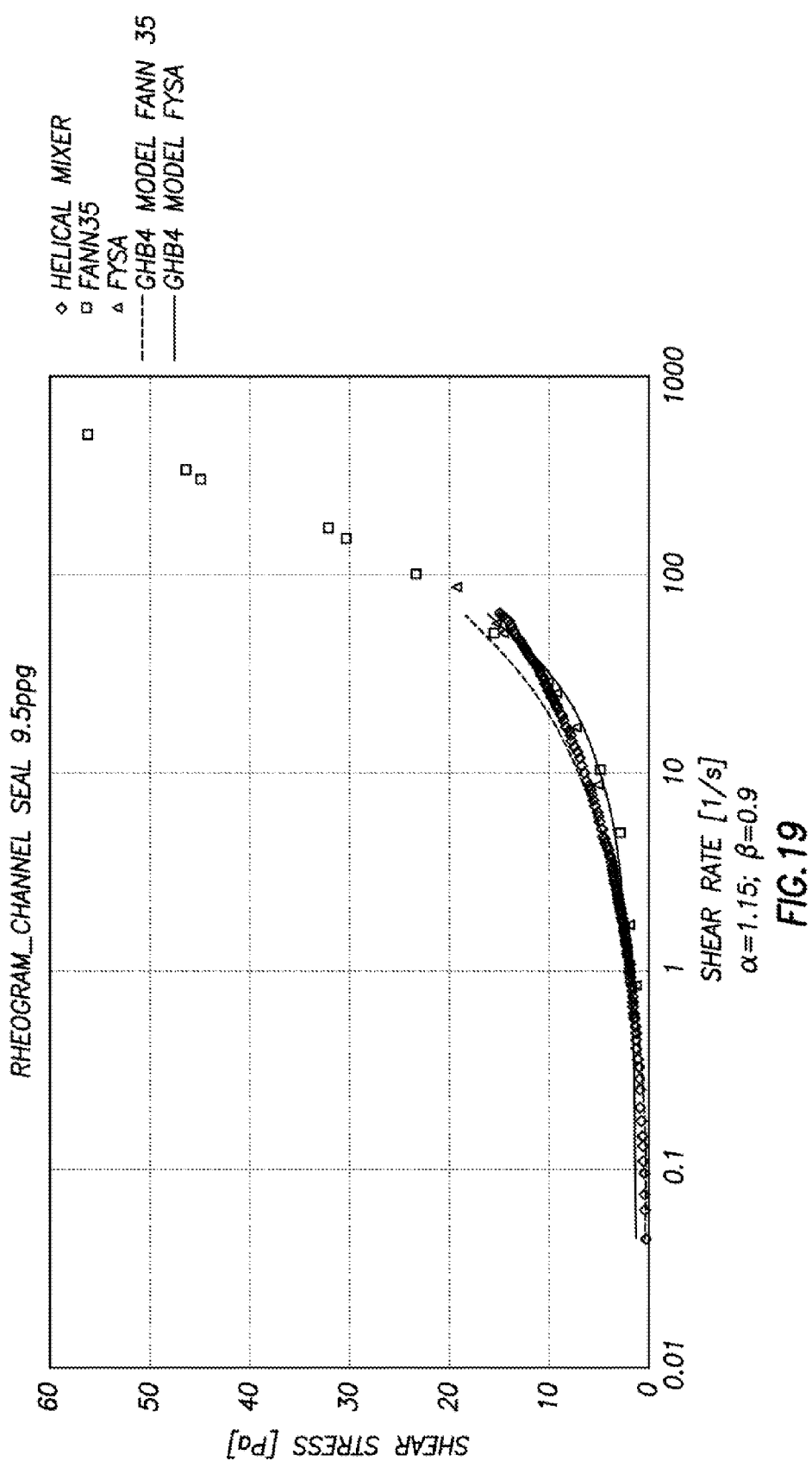
Figure 20:
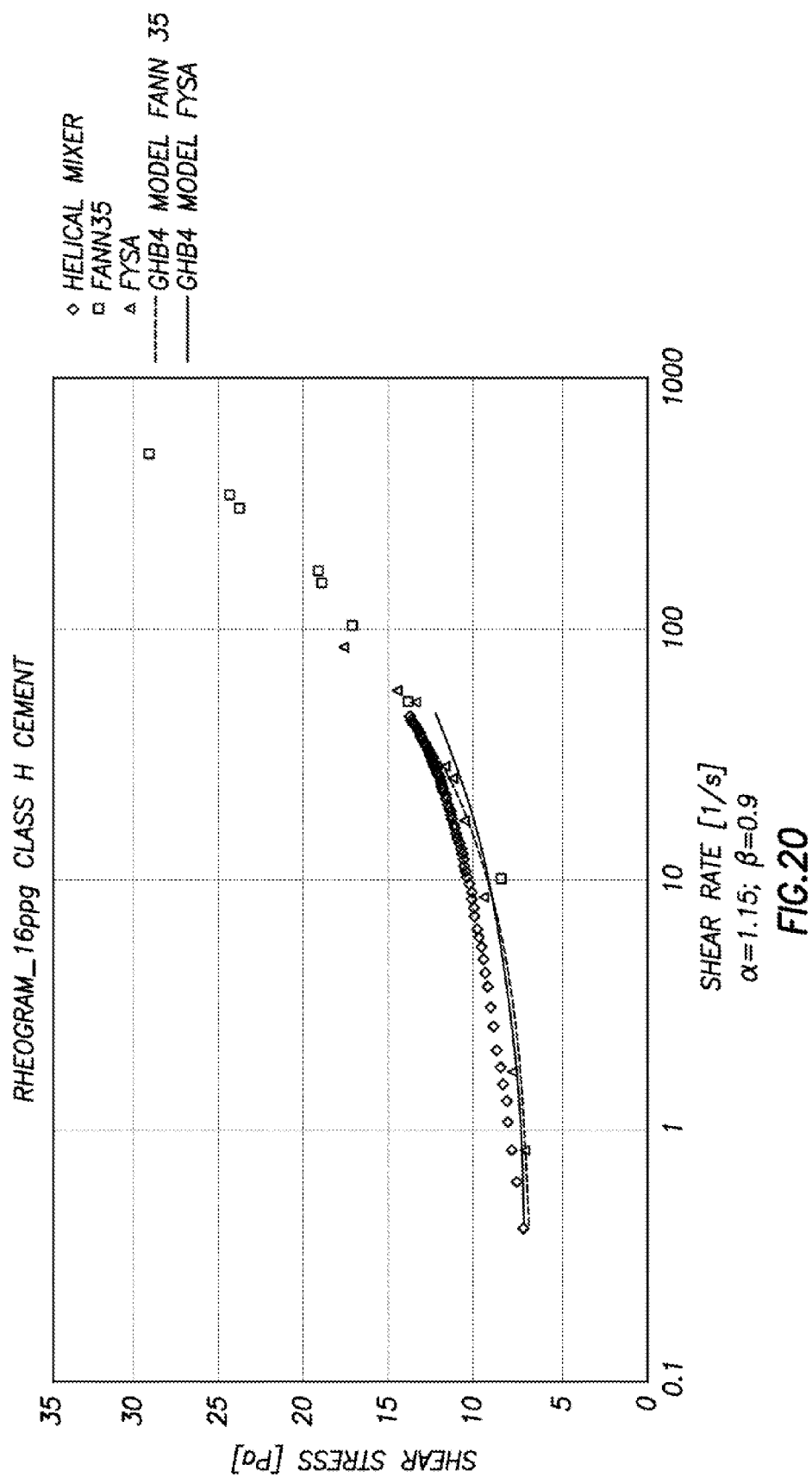
Figure 21:
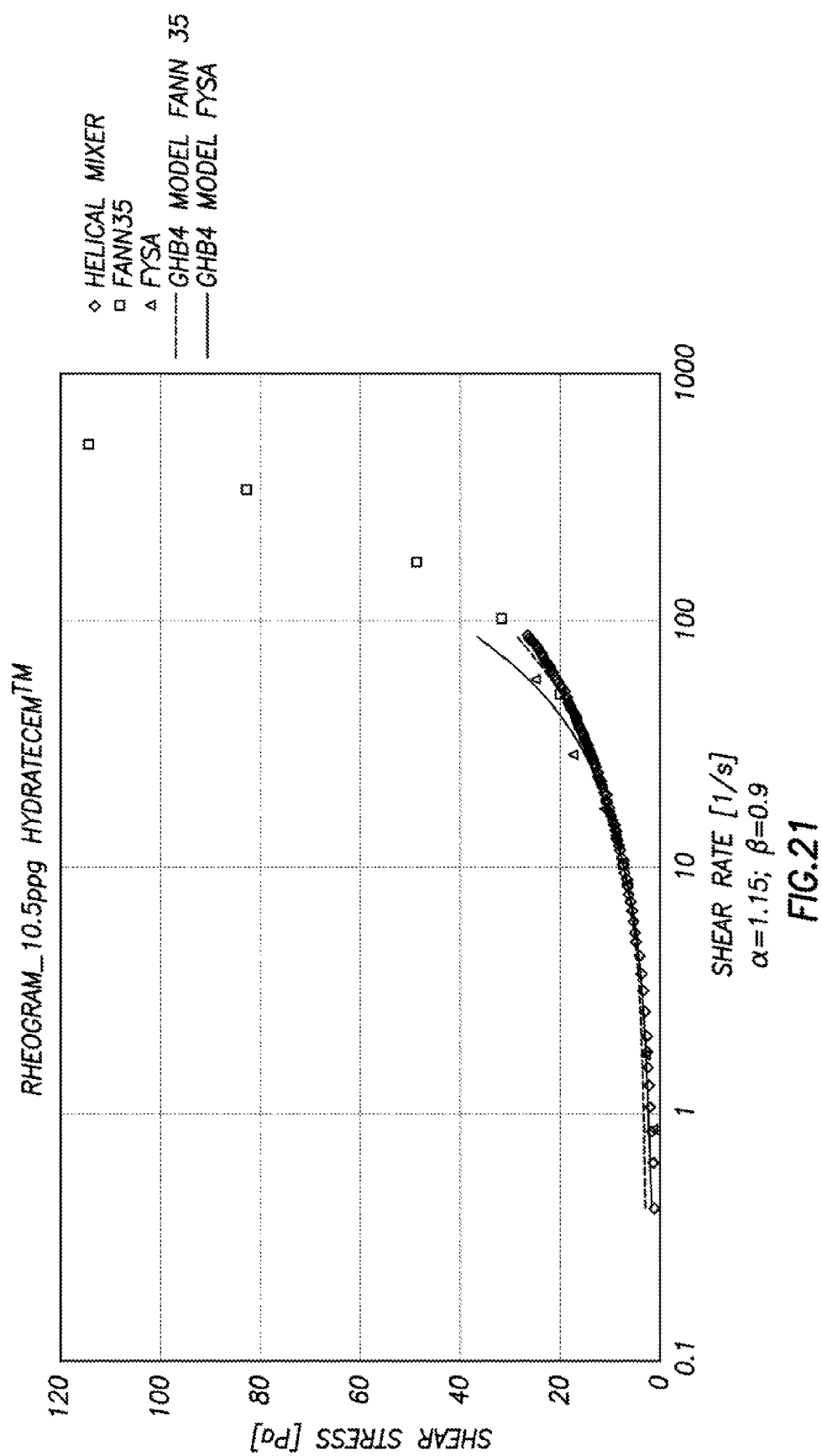
Figure 22:
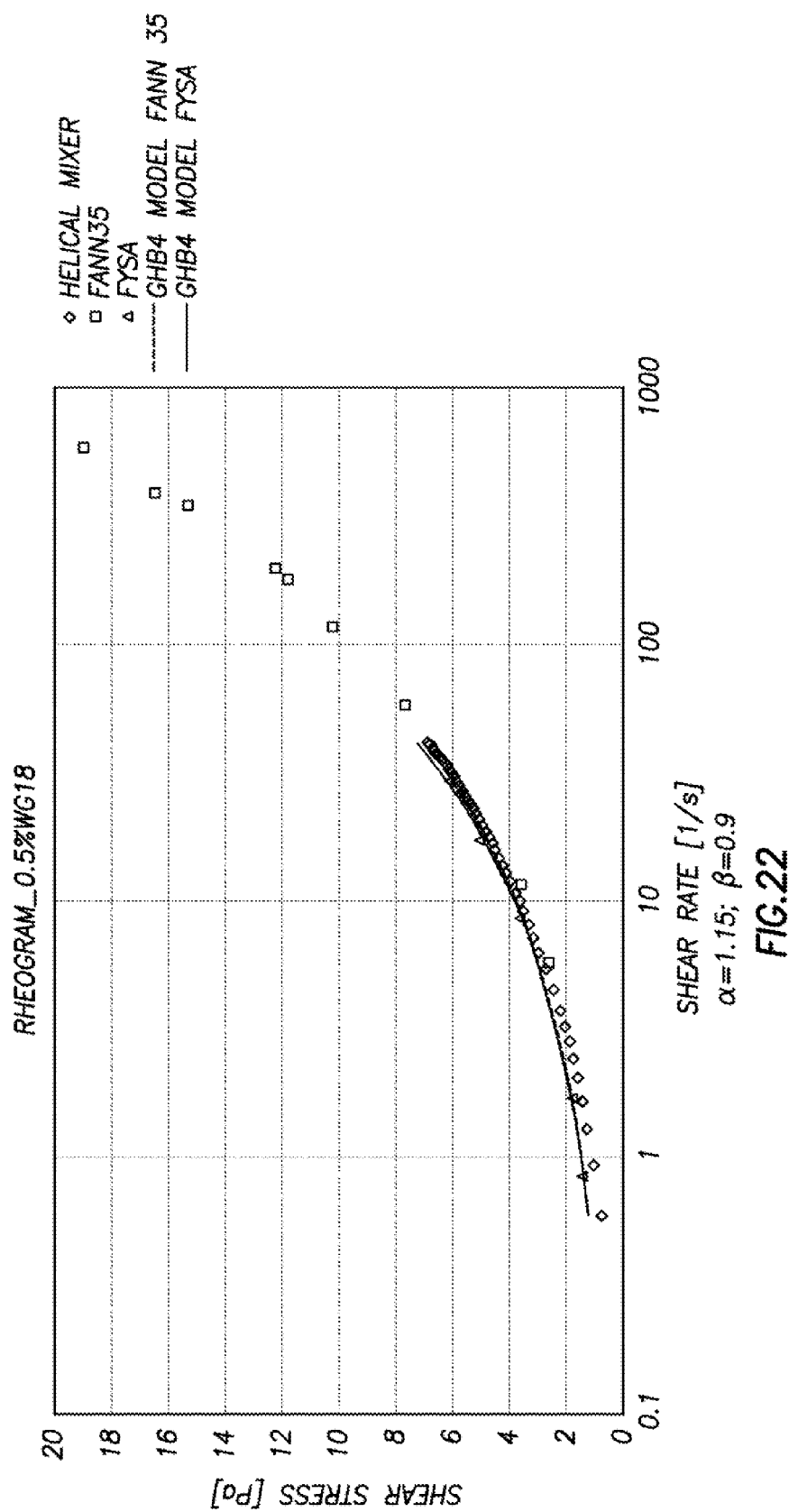
Figure 23:
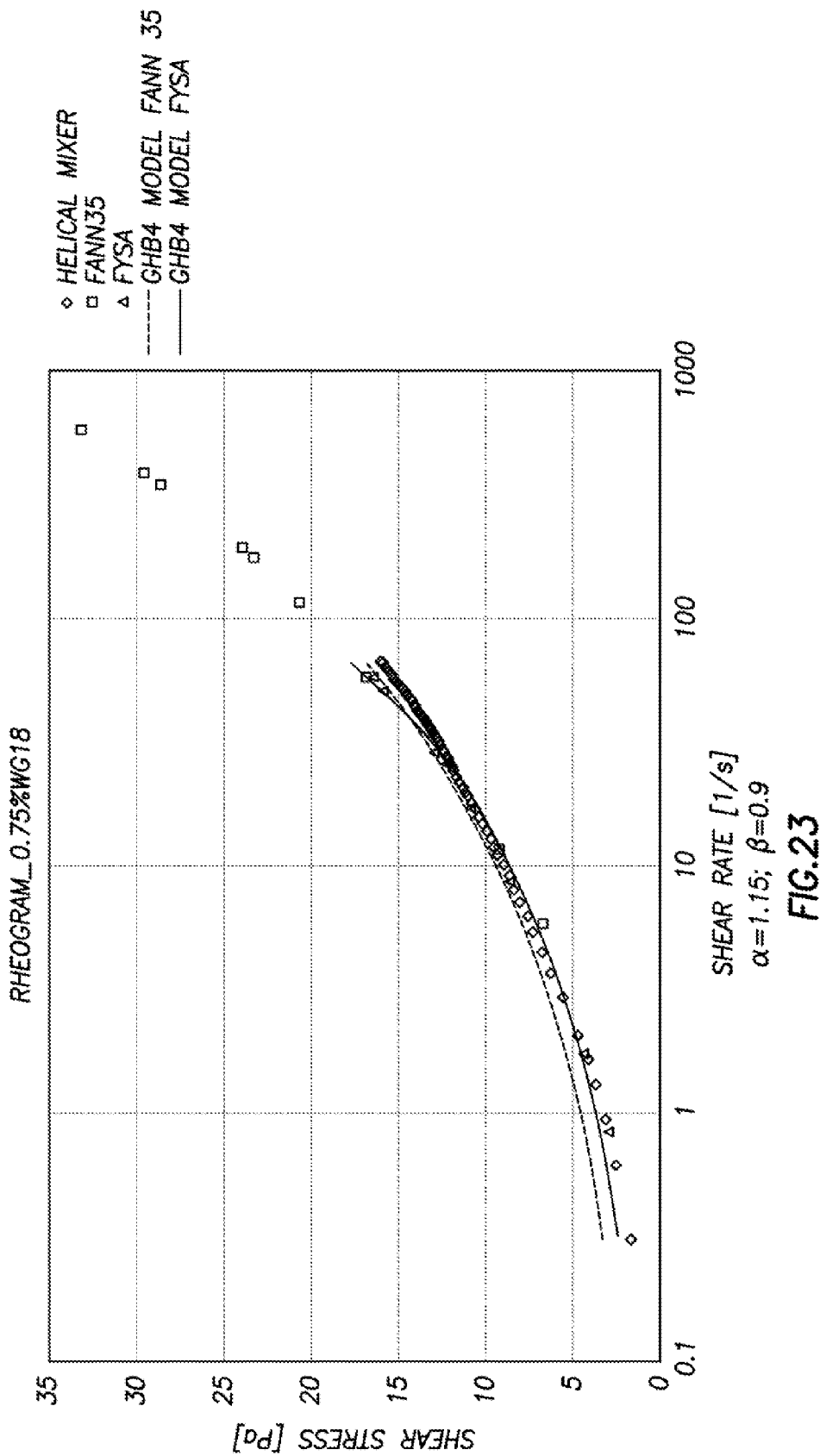

A consolidated similitude analysis for Newtonian fluids is shown in FIG. 13. It was observed that the nature of this curve starts deviating from a straight line relationship at $N_{Re,I}$≈200 which marks the onset of transitional flow. Hence all the data points where $N_{Re,I}$>200 were eliminated, as shown in FIG. 14.

Matching viscosity protocol for GHB-4 fluids:

1. Collect Torque vs. RPM data
2. d=0.05 m, A=6.9863, B=−0.98227, k1=0.158, K=5.78E-4

Start with an initial guess of α and β that is valid for Newtonian fluids, say, α=1 and β=1

$$3.\ \text{Determine}\ N_{Po} = (T^*\Omega)/(\Omega^{3*}d^{5*}\rho) \quad (17)$$

$$4.\ \text{Determine}\ N_{Re,I} = (N_{Po}/A)^{(1/B)} \quad (18)$$

5. Eliminate $N_{Re,I}$>=200

$$6.\ \text{Calculate}\ SR = k1^*(\Omega)^\alpha \quad (19)$$

$$SS = T^\beta/K \quad (20)$$

7. Plot rheogram and Van wazer plot. Eliminate low RPM data as per Van wazer plot
8. Take Fann-35 data for same fluid
   a. Eliminate low RPM data
   b. Eliminate turbulent data from visual inspection
   c. Fit Best Rheology GHB-4 model using k1_Fann=1.705 (1.94 for WG 18—by using Krieger Correction Factor for polymer solutions) k2_Fann=0.5099 (preferably, a Best Rheology GHB-4 model, proprietary to Halliburton Energy Services, is used, but other models may be used, if desired)
   d. Determine $\tau_0$, $\mu_\infty$, m, n
   e. Call this Model-I
9. Take FYSA data for same fluid.
10. Repeat steps 8(*a*) to 8(*d*). Call this Model-II.
11. Take SR values as determined from rheometer 20
   a. Apply Model-I→SS, estimated F-35 (GHB-4-F-35)
   b. Apply Model-II→SS, estimated FYSA (GHB-4-FYSA)

12. Calculate $$a.\ RSQ1=[(SS\_GHB\text{-}4\text{-}F\text{-}35)-(SS,helical)]^2 \qquad (21)$$

$$b.\ RSQ2=[(SS\_GHB\text{-}4\text{-}FYSA)-(SS,helical)]^2 \qquad (22)$$

$$c.\ RSQ3=[(SS\_GHB\text{-}4\text{-}FYSA)-(SS\_GHB\text{-}4\text{-}F\text{-}35)]^2 \qquad (23)$$

$$d.\ RMSRQ=[(RSQ1)^2+(RSQ2)^2]^{1/2} \qquad (24)$$

e. Survival criteria is
   i. RMSRQ is minimum, or
   ii. RSQ1<RSQ3, or
   iii. RSQ2<RSQ3

13. Optimize $\alpha$ and $\beta$ globally so that survival criteria is achieved for all fluids being tested.

It can be concluded from the experimentation with the rheometer 20 that:

1) A comprehensive similitude analysis of mixer torque-speed response data for Newtonian Fluids whose viscosities ranged from 10 cP to 1000 cP confirmed the following relationship between Power Number and Reynolds Number with respect to the rotor, $$N_{Po}=A(N_{Re\_I})^B \qquad (25)$$

2) The onset of transitional flow was observed to happen at $N_{Re,I}$~200

3) The mixer coefficients were determined as A=6.9863, B=−0.98227, d=0.05 (in SI Units)

4) Shear thinning index of the fluids studied was in the range of 0.265 to 0.815. Various empirical models were tried to fit the data.

$$\text{Volume Averaged Shear Rate } VASR[1/\text{sec}]=k1*(RPM)^\alpha \qquad (32)$$

$$\text{Shear Stress } SS[Pa]=T/K \qquad (33)$$

where Torque (T) is in N-m, k1=0.158, K=5.768E-4, $\alpha$=1.15

In all 20 fluid compositions that are used to service wellbores were studied. These included Linear polymer gels, water based drilling fluids, oil based drilling fluids, spacer compositions, cement slurries and settable spottable fluids. For example, by using the model in 4) the value of K was not constant for all fluids and had to be changed on a case to case basis to meet survival criteria as set in the data analysis protocol as above.

5) After using various models, it was found out that model mentioned in 6) fitted for all the fluids studied.

6) For the particle laden Non-Newtonian or GHB 4 fluids the Torque-Speed response obtained can be converted to meaningful rheology data by using the equations,
   Volume Averaged Shear Rate VASR[1/sec]=k1*(RPM)$^\alpha$
   Shear Stress SS[Pa]=T[N-m]$^\beta$/K
   where k1=0.158, K=5.768E-4, $\alpha$=1.15 and $\beta$=0.9

7) The rheometer 20 proves to be a very promising device to measure the rheological properties of particle laden fluids and the finite yield point of GHB4 fluids and low end rheology more accurately than existing rheometric systems.

A few of the rheograms that illustrate the excellent match between the GHB 4 models on Fann 35 and FYSA with the experimental results on the helical mixer are shown in FIGS. 15-23.

Example 1

Incompatibility Study 14 ppg dual spacer and 16 ppg Class H cement slurry form an incompatible mixture. Incompatibility study of the same mixture was carried out in the rheometer 20. The following procedure was carried out for the incompatibility study:

1. Cement slurry and Dual spacer were prepared as per American Petroleum Institute (API) practices.
2. Torque vs. RPM data was generated for Cement slurry as well for Dual spacer (see experimental procedure for Haake described above).
3. Similarly Torque vs. RPM data was generated for Dual spacer.
4. Cement slurry and Dual spacer were mixed in 25:75 volume percent.
5. Torque vs. RPM data was generated for this mixture.
6. Cement slurry and Spacer were mixer separately and then the mixture was used to generate Torque vs. RPM data.
7. Rheograms and Van wazer plots for 100% Cement, 100% Dual Spacer™ and mixture of 75% Spacer+25% Cement slurry were compared.
8. Rheogram for mixture of 75% Spacer+25% Cement slurry was shifted upwards as compared to 100% Cement, 100% Dual Spacer™.

Figure 24:
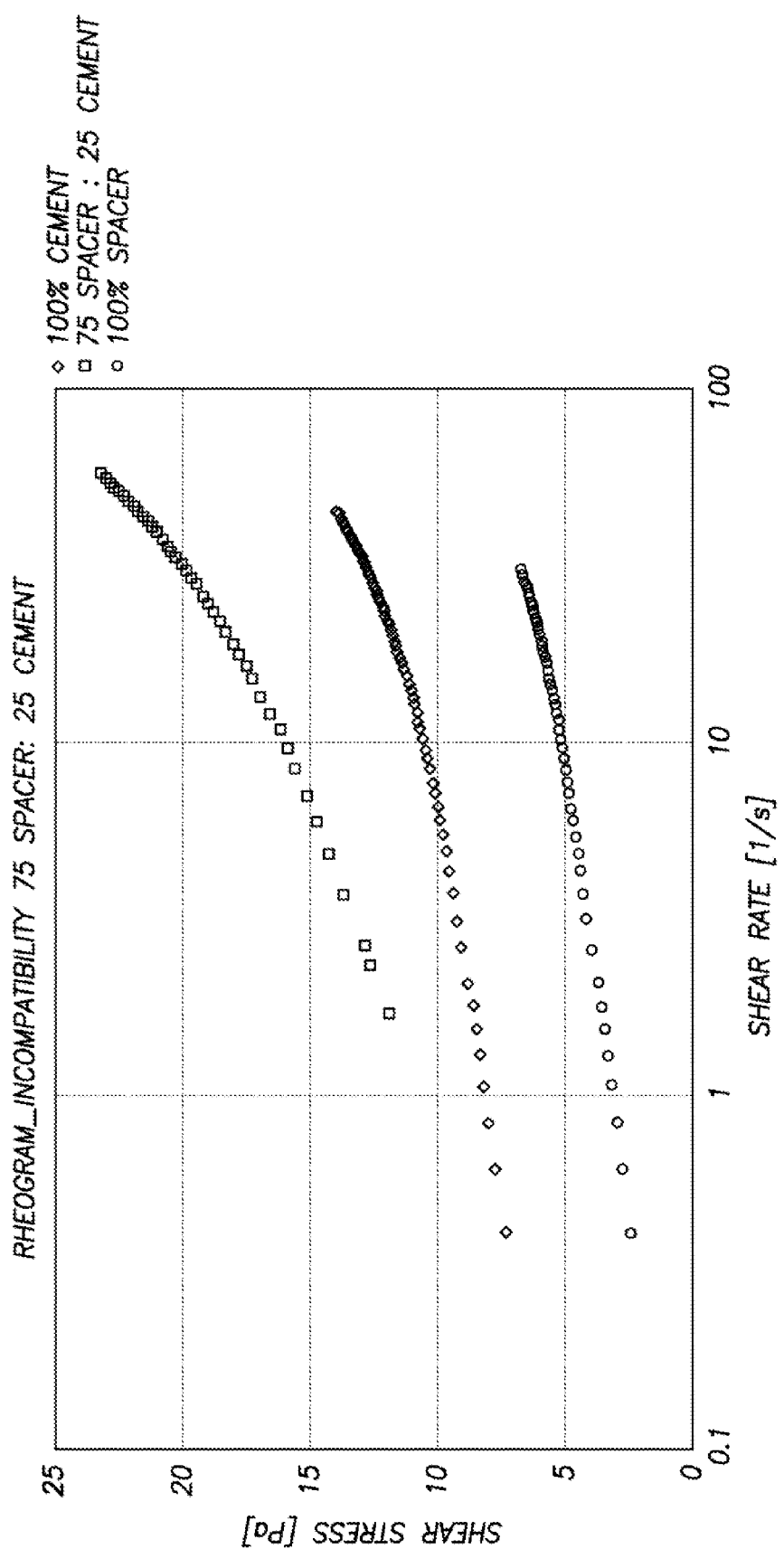
FIGS. 24 & 25 are plots of experimental results for a fluid incompatibility study.
Figure 25:
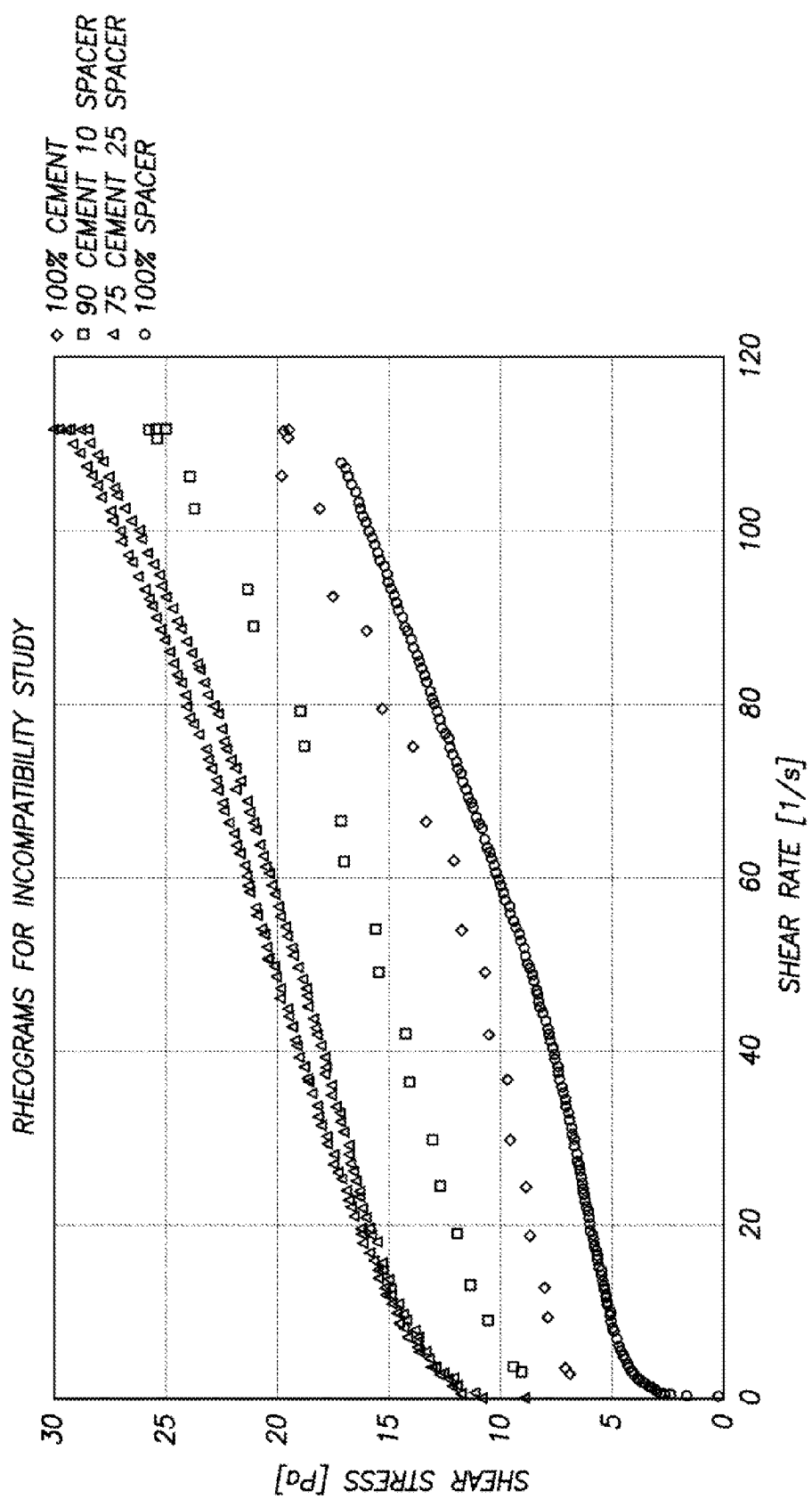

Results of this incompatibility study are shown in FIGS. 24 & 25.

Example 2

Figure 26:
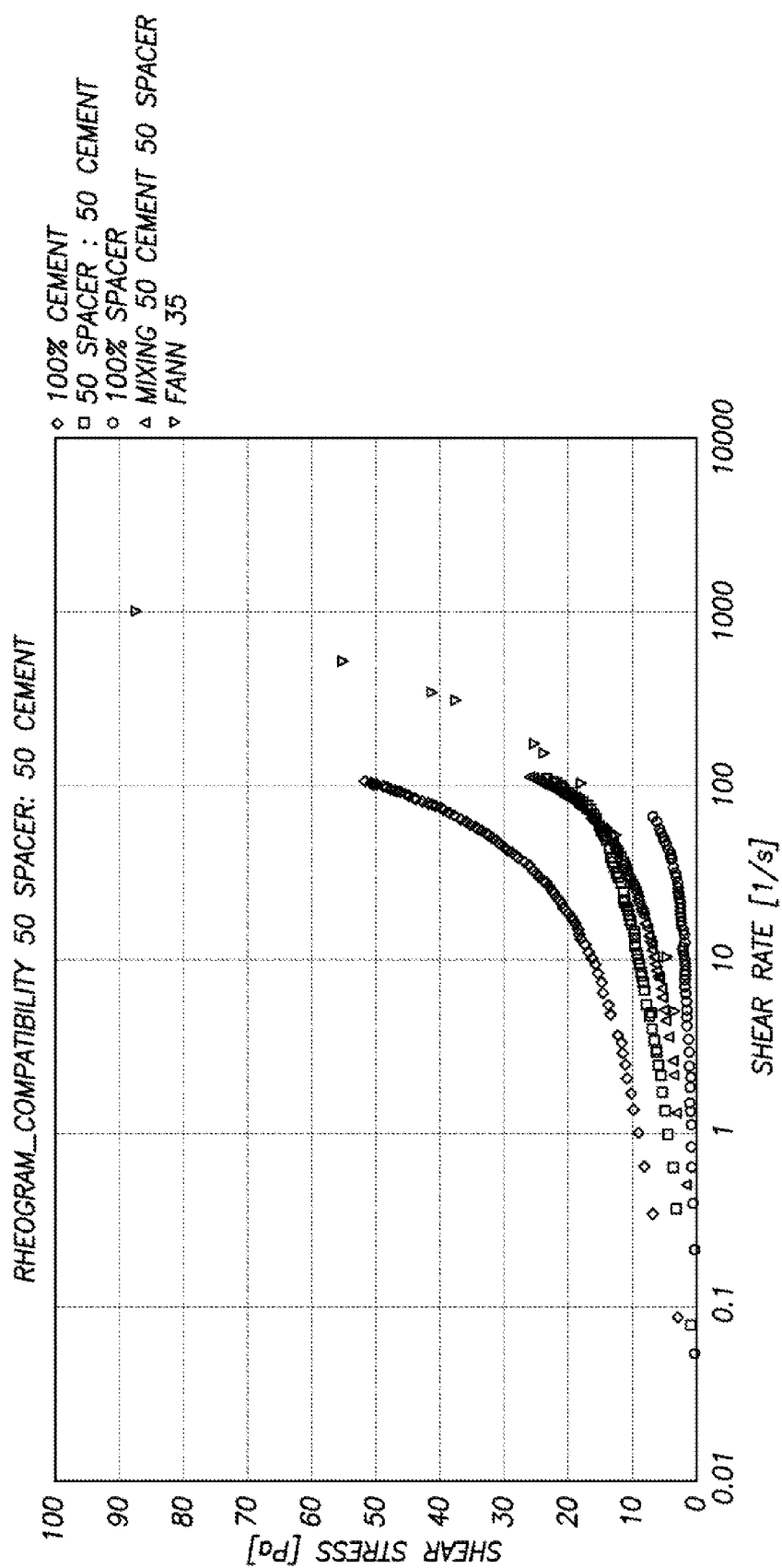
FIG. 26 is a plot of experimental results for a fluid compatibility study.

Compatibility Study 12 ppg Tuned Spacer E+(™) from Halliburton Energy Services and 16 ppg Class H cement slurry form a known compatible mixture. Compatibility study of the same mixture was carried out in the rheometer 20. The following procedure was carried out for the compatibility study:

1. Cement slurry and Tuned spacer E+ were prepared as per API practices.
2. Torque vs. RPM data was generated for Cement slurry as well for Tuned spacer E+ (e.g., see procedure for Haake described above).
3. Similarly, Torque vs. RPM data was generated for Tuned Spacer E+.
4. Cement slurry and Tuned Spacer E+ were mixed in 25:75 volume percent.
5. Torque vs. RPM data was generated for this mixture.
6. Cement slurry and Tuned Spacer E+ were mixed separately and then the mixer was used to generate Torque vs. RPM data
7. Rheograms and Van wazer plots for 100% Cement, 100% Tuned Spacer E+ and mixture of 50% Tuned Spacer E++50% Cement slurry were compared.
8. Torque vs. RPM data was generated by placing cement slurry initially in the stator, and the required quantity of Tuned spacer E+ was added at the top of the cement slurry. In situ mixing was done by the rheometer 20 itself. This data is compared with separately mixed cement slurry and tuned spacer E+, as shown in FIG. 26.

Example 3

Small Helical Rotor (SHR)

For capturing the rheology of particle laden fluids (e.g., a slurry), it is necessary to maintain the homogeneity of the slurry. This means that liquid motion during the rheological measurement should be such that fluid will travel from the bottom to the top of the receptacle in which the fluid is contained. Such motion of fluid will ensure that particles, present in the slurry, will not settle down and such motion will maintain the homogeneity of the slurry.

Keeping this in mind, a rapid prototype unit of the small helical rotor was prepared. This helical rotor can be fitted on the Fann 35 unit as a replacement for the standard bob. Sleeve (R1) can be used for this bob by closing its bottom.

SHR was calibrated using the procedure below:

Calibration Procedure

Two fluids will be needed during the calibration process. Fluid A is a known viscosity standard. Common Newtonian calibration oils work the best. Prefer to use 1000 cP, with 500 cP good as well. Minimum value should be 250 cP. Fluid B is a fracturing gel. 1% solution (by weight in water) of WG-18 is preferred (e.g., 4.8 grams of WG-18 in 500 grams of water). Mix in blender at 2000 rpm for 10 minutes, to allow full hydration.

1.) Fluid A (Newtonian standard) data was collected on a properly installed SHR. There was no need to perform "decay" tests, as Newtonian fluids do not exhibit yield points.

2.) Fluid B data was collected on both the standard Bob/Sleeve and the SHR.

3.) The calibration was performed by matching the slopes of the rheograms generated by SHR and a standard bob/sleeve configuration, and the k1 and k2 values are calculated.

Figure 27:
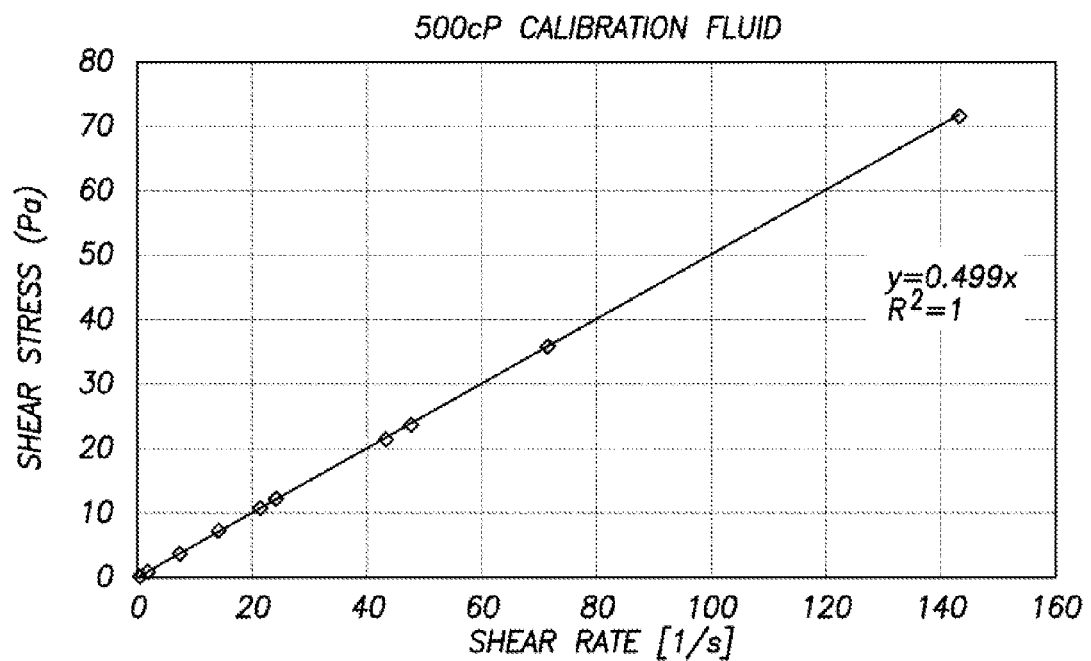
FIGS. 27-28 are calibration plots of experimental data for estimation of constants k1 and k2 for a rheometer with a small helical rotor.
Figure 28:
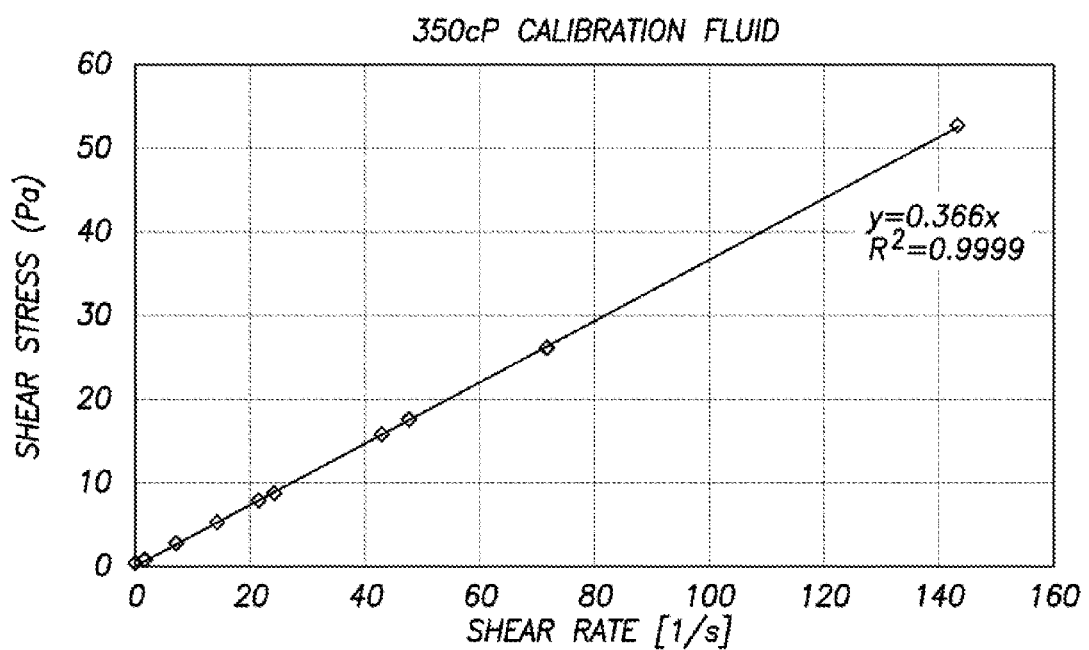

RPM vs. dial Reading data is generated as per the procedure given above. In this case, k1=0.239 k2=0.65. Results are shown in FIGS. 27 & 28.

Example 4

Yield Point Measurement

Yield point measurement was done for the shaving foam using Rheometer 20, FYSA and SHR.

Experimental & calculation Procedure for FYSA and SHR:

1. The experimental procedure described above for generating Dial reading vs. RPM data for Fann 35, was used for FYSA as well as SHR.

2. Additionally, 3 rpm and 6 rpm decay readings were taken for both FYSA and SHR.

3. Yield point was determined using Best Rheology spreadsheet (or other suitable yield point lookup table) for FYSA as well as SHR.

Experimental & calculation Procedure for Rheometer 20:

1. The experimental procedure described above for the Rheometer 20 was followed.

2. Yield point measurement was done by measuring torque requirement at constant speed of 0.5 rpm.

3. Maximum torque in the Torque vs. time curve for the rheometer 20 is used to calculate the yield point.

4. A constant used to convert torque to shear stress is used to calculate yield point from torque.

Figure 29:
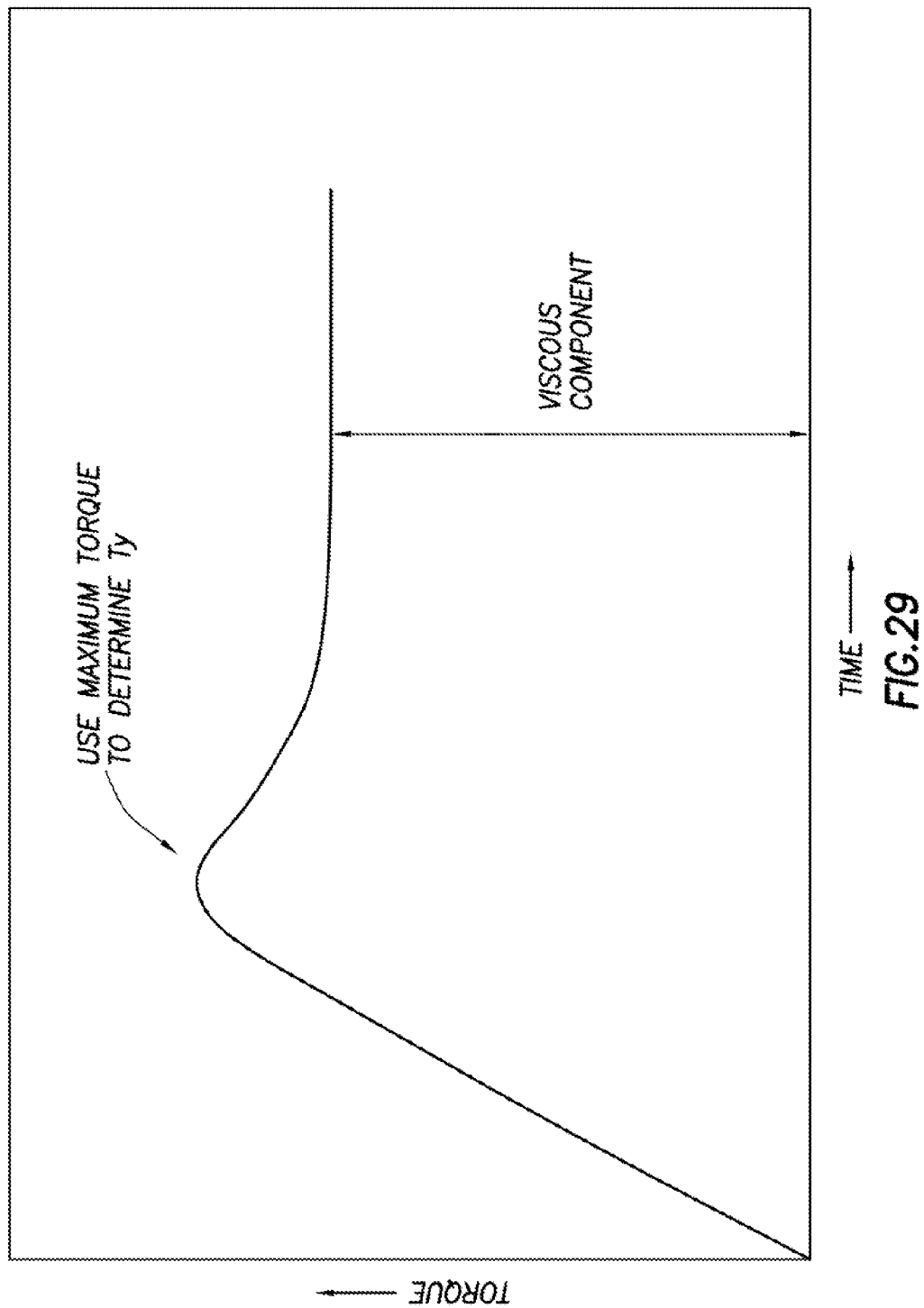
FIG. 29 depicts a Torque reading that is to be used to calculate Yield Point using helical mixer geometries.

A resulting graph is represented in FIG. 29.

Best Rheology gives the yield point for FYSA and SHR as follows.

| YP by FYSA | 17.008 Pa | i.e. 35.522 lbf/100 ft² |
|---|---|---|
| YP by SHR | 16.4961 Pa | i.e. 34.453 lbf/100 ft² |

YP in Rheometer 20

In the rheometer 20, the maximum torque required to start the flow is 10 mN-m. A model for converting Torque to shear stress for Rheometer 20 is:

$$\text{Shear Stress } SS[\text{Pa}] = T^\beta / K \quad (36)$$

where Torque is in N-m, K=5.768E-4, β=0.9

Case A: β=0.9, Yield point=27.48 Pa (i.e., 57.39 lbf/100 ft²)

Case B: β=1.0, Yield point=17.34 Pa (i.e., 36.21 lbf/100 ft²)

From above calculations, it becomes clear that coefficient β is related to the non-Newtonian flows in the system. Since at yield point, fluid is static and after YP fluid starts to flow. Hence for YP calculations, β is equal to 1.0.

Flow patterns in Rheometer 20 were investigated experimentally. A thick paste of wheat flour was prepared. It was then poured in the rheometer 20. The objective was to check the velocity profiles of the fluid inside the rheometer 20. It was found that the wheat flour paste was transferred rapidly from the bottom to the top, and laterally. This was inline with the observations from the computational fluid dynamics simulations.

It can be concluded from the experimentation conducted to date on the rheometer 20 that:

1) A comprehensive similitude analysis of mixer torque-speed response data for Newtonian Fluids whose viscosities ranged from 10 cP to 1000 cP confirmed the following relationship between Power Number and Reynolds Number with respect to the rotor:

$$N_{Po} = A(N_{Re\_J})^B \quad (37)$$

2) The onset of transitional flow was observed to happen at $N_{Re\_J} \sim 200$ 3) The mixer coefficients were determined as A=6.9863. B=−0.98227, d=0.05 (in SI Units)

4) Since there was correction required for the β value for some fluids, the model for estimation of Shear stress was rectified. The new model fits all the non-Newtonian fluids studied, e.g., linear gels, cement slurries, spacers, water based mud, oil based mud and viscoelastic fluid. The new model is given below:

$$\text{Volume Averaged Shear Rate } VASR[1/\text{sec}] = k1 * (RPM)^\alpha \quad (38)$$

$$\text{Shear Stress } SS[\text{Pa}] = T^\beta / K \quad (39)$$

where Torque is in N-m, k1=0.158, K=5.768E-4, α=1.15 and β=0.9

5) The range of shear thinning indices of the fluids studied was from 0.265 to 0.815.

6) The rheometer 20 proves to be a very promising device to measure the rheological properties of particle laden fluids, the finite YP of GHB4 fluids and low end rheology more accurately than existing rheometric systems.

7) Incompatibility studies can be carried out over a range of shear rate values. When fluid mixture is incompatible and gels up on mixing, torque requirement of the mixture is increased as compared to individual fluids. Increase in the torque requirement can be accurately captured by the rheometer 20 (which can be seen from the data of incompatible system of Class H cement and Dual spacer in FIGS. 24 & 25).

8) Since the mixture of Class H Cement slurry and Dual Spacer is a rheologically dynamic system, time required for mixing could not be estimated.

9) To estimate the time required for the mixing in the rheometer 20, system of compatible mixture will be used.

10) The rheometer 20 is able to capture the compatibility of two fluids

11) The rheometer 20 is able to mix and measure the Rheology well.

12) Yield point measurement can be done using the rheometer 20.

13) YP values obtained by rheometer 20 are comparable with the YP values obtained by FYSA and SHR.

14) An important point is that coefficients (Alpha=1.15 and Beta=0.9) are not required to convert torque to Shear stress.

It may now be fully appreciated that the above disclosure provides improvements to the art of rheological testing. In examples described above, the rheometer 20 includes helical blades 30 which effectively homogenize admixed fluids, and which consistently shear the fluids between the blades. Shear thinning indices do not need to be known beforehand, in order to calculate shear stress and shear rate from the torque-RPM data collected using the rheometer 20.

For rheology during flow we have VASR=k1*(RPM$^\alpha$) and Shear Stress=(Torque$^\beta$)/K. However, $\alpha$ and $\beta$ should be 1 and 1, respectively, for deducing gel strength information, compared to 1.15 and 0.9, respectively, for rheology during flow.

The helical mixer (rheometer 20) is more sensitive, in the sense that it does a better job of capturing shear stress information at low end shear rates (e.g., an order of magnitude less than conventional mixers). For example, if the lower limit of shear rate for gel strength measurements on a conventional mixer is 0.1 sec$^{-1}$, the rheometer 20 described herein could with ease handle 0.01-0.001 sec$^{-1}$ when rotated at lower RPM's, while maintaining fluid homogeneity and preventing wall slip.

A method of determining rheological properties of at least one fluid is described above. The method can include dispensing the at least one fluid into a rheometer including a stator having at least one helical blade; measuring torque (T) due to relative rotation between the stator and a rotor of the rheometer at different rotational speeds (RPM's); calculating shear stress (SS) as follows: SS=T$^\beta$/K; and calculating volume averaged shear rate (VASR) as follows: VASR=k1*RPM$^\alpha$, where K, k1, $\alpha$ and $\beta$ are experimentally-derived coefficients.

Coefficients $\alpha$ and $\beta$ can be independent of a shear thinning index of the fluid.

The rotor can be helical shaped.

In the method, A can equal $10^{Intercept}$, where Intercept is an abscissa intercept of a plot of $\log(N_{Po})$ vs. $\log(N_{Re})$, and where $N_{Po}$ is a power number and $N_{Re}$ is a Reynolds Number for flow with respect to the rotor.

In the method, wherein B can equal a slope of the plot of $\log(N_{Po})$ vs. $\log(N_{Re})$.

In the method, $\log(N_{Po})$ vs. $\log(N_{Re})$ may be plotted only for a laminar regime to experimentally determine K, k1, $\alpha$ and $\beta$.

K, k1, $\alpha$ and $\beta$ can be determined using a matching viscosity protocol by minimizing errors between rheograms from two or more different geometries (such as Fann 35 & FYSA, etc.).

In one example, a rheometer 20 is described which includes a stator 28 having at least one first helical blade 30b, and a rotor 26 having at least one second helical blade 30a.

The first and second helical blades 30a,b can have a substantially same pitch and/or curvature. The first helical blade 30b may comprise a portion of a helix 50.

The first helical blade 30b may be spaced apart from the second helical blade 30a by a substantially constant gap 44.

Multiple first helical blades 30b can be helically spaced apart on a cylindrical surface 32 of the stator 28. Multiple second helical blades 30a can be axially spaced apart on the rotor 26.

Also described above is a method of mixing fluids 12, 14 and performing a rheological test on the admixed fluids. The method can include dispensing a first fluid 12 into a rheometer 20, then dispensing a second fluid 14 into the rheometer 20, then mixing the first and second fluids 12, 14 with at least one helical blade 30 of the rheometer 20, and then measuring torque due to relative rotation between a stator 28 and a rotor 26 of the rheometer 20.

The stator 28 and/or the rotor 26 may comprise the helical blade 30. The at least one helical blade may include at least one first helical blade 30b on the stator 28 and at least one second helical blade 30a on the rotor 26.

A rotary rheometer 20 is also provided to the art by this disclosure. The rheometer 20 can include a rotor 26, and a stator 28 having at least one first helical blade 30b. Multiple first helical blades 30b may be helically spaced apart on the stator 28.

The rotor 26 may include at least one second helical blade 30a. The first and second helical blades 30a,b may be spaced apart from each other by a substantially constant gap 44. The first and second helical blades 30a,b may have a substantially same pitch and/or curvature.

It is to be understood that the various examples described above may be utilized in various orientations, such as inclined, inverted, horizontal, vertical, etc., and in various configurations, without departing from the principles of this disclosure. The embodiments illustrated in the drawings are depicted and described merely as examples of useful applications of the principles of the disclosure, which are not limited to any specific details of these embodiments.

In the above description of the representative examples, directional terms (such as "above," "below," "upper," "lower," etc.) are used for convenience in referring to the accompanying drawings. However, it should be clearly understood that the scope of this disclosure is not limited to any particular directions described herein.

Of course, a person skilled in the art would, upon a careful consideration of the above description of representative embodiments, readily appreciate that many modifications, additions, substitutions, deletions, and other changes may be made to these specific embodiments, and such changes are within the scope of the principles of this disclosure. Accordingly, the foregoing detailed description is to be clearly understood as being given by way of illustration and example only, the spirit and scope of the invention being limited solely by the appended claims and their equivalents.

What is claimed is:

1. A method of determining rheological properties of at least one fluid, the method comprising:
   dispensing the at least one fluid into a rheometer including a stator having at least one first helical blade and a rotor having at least one second helical blade;
   measuring torque (T) due to relative rotation between the stator and the rotor of the rheometer at different rotational speeds (RPM's);
   calculating shear stress (SS) as follows: SS=T$^\beta$/K; and
   calculating volume averaged shear rate (VASR) as follows: VASR=k1*RPM$^\alpha$,
   where K, k1, $\alpha$ and $\beta$ are experimentally-derived coefficients.

2. The method of claim 1, wherein coefficients $\alpha$ and $\beta$ are independent of a shear thinning index of the fluid.

3. The method of claim 1, wherein the at least one first helical blade intermeshes with the at least one second helical blade during relative rotation between the stator and the rotor.

4. The method of claim 1, wherein log Power number ($N_{Po}$) vs. log Reynolds number ($N_{Re}$) is plotted only for a laminar regime to experimentally determine K, k1, $\alpha$ and $\beta$.

5. The method of claim 1, wherein K, k1, $\alpha$ and $\beta$ are determined using a matching viscosity protocol by minimizing discrepancies between rheograms from two or more different rheometer geometries.

6. A method of mixing fluids and performing a rheological test on the admixed fluids, the method comprising:
 dispensing a first fluid into a rheometer including a stator having at least one first helical blade and a rotor having at least one second helical blade;
 then dispensing a second fluid into the rheometer;
 then mixing the first and second fluids in the rheometer; and
 then measuring torque due to relative rotation between the stator and the rotor of the rheometer.

7. The method of claim 6, wherein the at least one first helical blade intermeshes with the at least one second helical blade during relative rotation between the stator and the rotor.

8. The method of claim 6, wherein the first helical blade is spaced apart from the second helical blade by a substantially constant gap.

9. The method of claim 6, wherein the at least one first helical blade comprises multiple first helical blades, and further comprising helically spacing apart the first helical blades on a cylindrical surface of the stator.

10. The method of claim 6, wherein the at least one second helical blade comprises multiple second helical blades, and further comprising axially spacing apart the second helical blades on the rotor.

* * * * *